US009931300B2

(12) United States Patent
Bilgili et al.

(10) Patent No.: US 9,931,300 B2
(45) Date of Patent: Apr. 3, 2018

(54) METHODS FOR SUPERDISINTEGRANT-BASED COMPOSITE PARTICLES FOR DISPERSION AND DISSOLUTION OF ACTIVE PHARMACEUTICAL AGENTS

(71) Applicant: New Jersey Institute of Technology, Newark, NJ (US)

(72) Inventors: Ecevit Bilgili, Woodbridge, NJ (US); Rajesh Dave, Princeton, NJ (US); Anagha Bhakay, Harrison, NJ (US); Mohammad Azad, Newark, NJ (US)

(73) Assignee: NEW JERSEY INSTITUTE OF TECHNOLOGY, Newark, NJ (US)

( * ) Notice: Subject to any disclaimer, the term of this patent is extended or adjusted under 35 U.S.C. 154(b) by 0 days.

(21) Appl. No.: 15/235,397

(22) Filed: Aug. 12, 2016

(65) Prior Publication Data

US 2016/0346209 A1 Dec. 1, 2016

Related U.S. Application Data

(62) Division of application No. 13/829,948, filed on Mar. 14, 2013, now Pat. No. 9,452,107.

(60) Provisional application No. 61/625,082, filed on Apr. 16, 2012.

(51) Int. Cl.

| | |
|---|---|
| *A61K 9/14* | (2006.01) |
| *A61J 3/00* | (2006.01) |
| *A61J 3/02* | (2006.01) |
| *A61K 9/51* | (2006.01) |
| *B82Y 40/00* | (2011.01) |
| *A61K 31/216* | (2006.01) |
| *A61K 31/343* | (2006.01) |
| *B05D 7/24* | (2006.01) |

(52) U.S. Cl.
CPC ............... *A61K 9/146* (2013.01); *A61J 3/00* (2013.01); *A61J 3/02* (2013.01); *A61K 9/5138* (2013.01); *A61K 9/5161* (2013.01); *A61K 31/216* (2013.01); *A61K 31/343* (2013.01); *B05D 7/24* (2013.01); *B82Y 40/00* (2013.01)

(58) Field of Classification Search
None
See application file for complete search history.

(56) References Cited

U.S. PATENT DOCUMENTS

| | | | |
|---|---|---|---|
| 5,145,684 | A | 9/1992 | Liversidge et al. |
| 5,275,824 | A | 1/1994 | Carli et al. |
| 5,858,410 | A | 1/1999 | Muller et al. |
| 6,074,670 | A | 6/2000 | Stamm et al. |
| 2010/0104637 | A1 | 4/2010 | Qiu et al. |

OTHER PUBLICATIONS

Bhakay, A., et al., Drug Development and Industrial Pharmacy 37(8): 963-976 (2011).*
Azad, M., et al., European Journal of Pharmaceutics and Biopharmaceutics 94: 372-385 (2015).*
Colombo, et al., Disintegrating Force and Tablet Properties, Drug Development and Industrial Pharmacy, 7(2), 135-153, 1981.
Hollenbeck, et al., Estimation of the Extent of Drug-Excipient Interactions Involving Croscarmellose Sodium, Journal of Pharmaceutical Sciences, vol. 72, No. 3, pp. 325-327, 1983.
Kamp, et al., Improvement by Super Disintegrants of the Properties of Tablets Containing Lactose, Prepared by Wet Granulation, Pharmaceutisch Weekblad Scientific Edition, vol. 5, pp. 165-171, 1983.
Colombo, et al., Disintegrating Force as a New Formulation Parameter, Journal of Pharmaceutical Sciences, pp. 701-705, 1984.
Gould, et al., The Effect of Recompression on the Swelling Kinetics of Wet Massed Tablets, Containing Super Disin, Drug Development and Industrial Pharmacy, vol. 11, No. 9-10, pp. 1819-1836, 1985.
Carli et al., Influence of Polymer Characteristics on Drug Loading Into Crospovidone, Int. J. Pharm. 33, 115-124, 1986.
Smidt, et al., Dissolution Kinetics of Griseofulvin in Sodium Dodecylsulphate Solutions, Journal of Pharmaceutical Sciences, vol. 76, pp. 711-714, 1987.
Hollenbeck, Bioavailability of Phenylpropanolamine HCl From Tablet Dosage Forms Containing Croscarmellose Sodium, International Journal of Pharmaceutics, 47, pp. 89-93, 1988.
Hintz, et al., The Effect of Particle Size Distribution on Dissolution Rate and Oral Absorption, International Journal of Pharmaceutics, 51, pp. 9-17, 1989.
Ploehn, et al., Interactions Between Colloidal Particles and Soluble Polymers, Advances in Chemical Engineering, vol. 15, pp. 137-228, 1990.
Martini et al., Physico-Chemical Characteristics of Steroid-Crosslinked Polyvinylpyrrolidone Coground Systems, Int. J. Pharm. 75, 141-146, 1991.
Gordon M., et al., Effect of the Mode of Superdisintegrant Incorporation on Dissolution in Wet Granulated Tablets, Journal of Pharmaceutical Sciences, 82, No. 2, 220-226, 1993.
Schubert, Instantization of Powdered Food Products, International Chemical Engineering, vol. 33, No. 1, pp. 28-45, 1993.

(Continued)

*Primary Examiner* — David J Blanchard
*Assistant Examiner* — Daniel F Coughlin
(74) *Attorney, Agent, or Firm* — McCarter & English, LLP

(57) ABSTRACT

The present disclosure provides improved systems and methods utilizing colloidal/ultrafine superdisintegrant-based composite particles for dispersion and/or dissolution of active pharmaceutical agents. In general, the present disclosure utilizes a surfactant-free or near surfactant-free formulation by incorporating a wet milled SDI as a dispersant in the formulation. As such, the present disclosure provides for the preparation of surfactant-free or substantially surfactant-free formulations (e.g., nano-composite micro-particle formulations) by incorporating a wet-milled superdisintegrant (SDI) as the dispersant in the formulations. The advantageous SDI particles (e.g., colloidal/ultrafine SDI particles) of the present disclosure can be used to break-up the aggregates (e.g., nanoparticle aggregates) of the active agents (e.g. poorly water-soluble drugs) in the formulations (e.g., micro-particle formulations) and enhance the recovery of the nanoparticles of active agents during aqueous re-dispersion and their dissolution rate in vitro and in vivo.

29 Claims, 19 Drawing Sheets

(56) References Cited

OTHER PUBLICATIONS

Liversidge et al., Particle Size Reduction for Improvement of Oral Bioavailability of Hydrophobic Drugs: I. Absolute Oral Bioavailability of Nanocrystalline Danazol In Beagle Dogs, International Journal of Pharmaceutics, 125, 91-97, 1995.
Fäldt, et al., Spray-Dried Whey Protein/Lactose/Soybean Oil Emulsions. 2. Redispersability, Wettability and Particle Structure, Food Hydrocolloids, vol. 10, No. 4, pp. 431-439, 1996.
Maa, et al., Spray-Coating of rhDNase on Lactose: Effect of System Design, Operational Parameters and Protein Formulation, International Journal of Pharmaceutics, 144, pp. 47-59, 1996.
Polli, et al., Methods to Compare Dissolution Profiles, Drug Informational Journal, vol. 30, pp. 1113-1120, 1996.
Thilbert, et al, Direct Visualization of Superdisintegrant Hydration Using Environmental Scanning Electron Microscopy, Communications, Journal of Pharmaceutical Sciences, vol. 85, No. 11, pp. 1255-1258, Nov. 1996.
De Villiers, Influence of Agglomeration of Cohesive Particles on the Dissolution Behaviour of Furosemide Powder, International Journal of Pharmaceutics, 136, pp. 175-179, 1996.
Bolhuis, et al., Improvement of Dissolution of Poorly Soluble Drugs by Solid Deposition on a Super Disintegrant. II. The Choice of Super Disintegrants and Effect of Granulation, European Journal of Pharmaceutical Sciences, 5, pp. 63-69, 1997.
Okimoto, et al., Dissolution Mechanism and Rate of Solid Dispersion Particles of Nilvadipine With Hydroxypropylmethylcellulose, International Journal of Pharmaceutics, 159, pp. 85-93, 1997.
Schwarz et al., Freeze-Drying of Drug-Free and Drug-Loaded Solid Lipid Nanoparticles (SLN), International Journal of Pharmaceutics, 157, pp. 171-179, 1997.
Sharma, et al., Effect of Nonadsorbing Polyelectrolytes on Colloidal Interactions in Aqueous Mixtures, Journal of Colloid and Interface Science, 191, pp. 236-246, 1997.
Freitas, et al., Spray-Drying of Solid Lipid Nanoparticles (SLN), European Journal of Pharmaceutics and Biopharmaceutics, 46, pp. 145-151, 1998.
Volker Buhler, Kollidon, Polyvinylpyrrolidone for the Pharmaceutical Industry, Mar. 1998 ($4^{th}$ Edition).
Muller R., et al., Nanosuspensions for the Formulation of Poorly Soluble Drugs: I. Preparation by a Size Reduction Technique, International Journal of Pharmaceutics, 160, 229-237, 1998.
Sallam, et al, Evaluation of Fast Disintegrants in Terfenadine Tablets Containing a Gas-Evolving Disintegrant, Drug Development and Industrial Pharmacy, 24(6), pp. 501-507, 1998.
Freudig, et al., Dispersion of Powders in Liquids in A Stirred Vessel, Chemical Engineering and Processing, 38, pp. 525-532, 1999.
Maggi, et al., Formulation of Biphasic Release Tablets Containing Slightly Soluble Drugs, European Journal of Pharmaceutics and Biopharmaceutics, 48, pp. 37-42, 1999.
Moline-Boisseau, et al., Fine Grinding of Polymers in a Vibrated Bead Mill, Powder Technology, 105, pp. 321-327, 1999.
Serajuddin, Solid Dispersion of Poorly Water-Soluble Drugs: Early Promises, Subsequent Problems, and Recent Breakthroughs, Journal of Pharmaceutical Sciences, vol. 88, No. 10, pp. 1058-1066, Oct. 1999.
Schmidt, et al., Incorporation of Polymeric Nanoparticles Into Solid Dosage Forms, Journal of Controlled Release, 57, pp. 115-125, 1999.
Chen et al., Gastric Retention Properties of Superporous Hydrogel Composites, Journal of Controlled Release, 64, pp. 39-51, 2000.
Grassi, et al., Drug Release From an Ensemble of Swellable Crosslinked Polymer Particles, Journal of Controlled Release, 68, pp. 97-113, 2000.
Jackson, et al., Drug-Excipient Interactions and Their Affect on Absorption, PSTT, vol. 3, No. 10, pp. 336-345, Oct. 2000.
Zimmermann, et al., Influence of Different Parameters on Reconstitution of Lyophilized SLN, International Journal of Pharmaceutics, 196, pp. 211-213, 2000.
Bilgili, et al., Pulverization of Rubber Granulates Using the Solid-State Shear Extrusion SSSE Process: Part I. Process Concepts and Characteristics, Powder Technology, 115, pp. 265-276, 2001.
Crowley et al., Drug Excipient Interactions, Pharmaceutical Technology, 6 pages, 2001.
Lopez-Solis et al., Effect of Disintegrants With Different Hygroscopicity on Dissolution of Norfloxacin/Pharmatose DCL 11 Tablets, International Journal of Pharmaceutics, 216, 127-135 2001.
Qureshi, et al., Cause of High Variability in Drug Dissolution Testing and Its Impact on Setting Tolerances, European Journal of Pharmaceutical Sciences, 12, pp. 271-276, 2001.
Levis, et al., Production and Evaluation of Size Reduced Grades of Microcrystalline Cellulose, International Journal of Pharmaceutics, 213, pp. 13-24, 2001.
Thibert, et al., The Effects of Milling Upon the Physicochemical Properties and Functional Behavior of Some Disintegrants, S.T.P. Pharma Sciences, 11, 2, pp. 123-128, 2001.
Berton, et al., Measurement of Hydration Capacity of Wheat Flour: Influence of Composition and Physical Characteristics, Powder Technology, 128, pp. 326-331, 2002.
Konan, et al., Preparation and Characterization of Sterile and Freeze-Dried Sub-200 nm Nanoparticles, International Journal of Pharmaceutics, 233, pp. 239-252, 2002.
Liang, et al., Production of Fine Polymer Powder Under Cryogenic Conditions, Chemical Engineering Technology, 25, 4, pp. 401-405, 2002.
Molina-Boisseau, et al., Characterisation of the Physicochemical Properties of Polymers Ground in a Vibrated Bead Mill, Powder Technology, 128, pp. 99-106, 2002.
Sonner, et al., Spray-Freeze-Drying for Protein Powder Preparation: Particle Characterization and a Case Study With Trypsinogen Stability, Journal of Pharmaceutical Sciences, vol. 91, No. 10, pp. 2122-2139, Oct. 2002.
Sunada, et al., Preparation, Evaluation and Optimization of Rapidly Disintegrating Tablets, Powder Technology, 122, pp. 188-198, 2002.
Vergote, et al., In vivo Evaluation of Matrix Pellets Containing Nanocrystalline Ketoprofen, International Journal of Pharmaceutics, 240, pp. 79-84, 2002.
Hogekamp, et al., Porosity Measurement of Fragile Agglomerates, Powder Technology, 130, pp. 385-392, 2003.
Lee, Drug Nano- and Microparticles Processed Into Solid Dosage Forms: Physical Properties, Journal of Pharmaceutical Sciences, 92, 2057-2068, 2003.
Rasenack, et al., Microcrystals for Dissolution Rate Enhancement of Poorly Water-Soluble Drugs, International Journal of Pharmaceutics, 254, pp. 137-145, 2003.
Shahgaldian, et al., A Study of the Freeze-Drying Conditions of Calixarene Based Solid Lipid Nanoparticles, European Journal of Pharmaceutics and Biopharmaceutics, 55, pp. 181-184, 2003.
Akka, et al., Solubilizing Poorly Soluble Antimycotic Agents by Emul Sification Via A Solvent-Free Process, AAPS PharmSciTech, 5(1) Article 24, pp. 1-6, 2004.
Hu, et al., Drug Development and Industrial Pharmacy, vol. 30, No. 3, pp. 233-245, 2004.
Sham, et al, Formulation and Characterization of Spray-Dried Powders Containing Nanoparticles for Aerosol Delivery to the Lung, International Journal of Pharmaceutics, 269, pp. 457-467, 2004.
Fujii et al., Preparation, Characterization, and Tableting of a Solid Dispersion of Indomethacin With Crospovidone, International Journal of Pharmaceutics, 293, 145-153, 2005.
Iida, et al., Preparation of Dry Powder Inhalation with Lactose Carrier Particles Surface-Coated Using A Wurster Fluidized Bed, Chemical Pharmaceutical Bulleting, 53(4), pp. 431-434, 2005.
Jeong et al., Effect of Cryoprotectants on the Reconstitution of Surfactant-Free Nanoparticles of poly(DL-lactide-co-glycolide), Journal of Microencapsulation, 22(6), pp. 593-601, 2005.
Kim et al., Preparation and Characterization of Solid Lipid Nanoparticles (SLN) Made of Cacao Butter and Curdlan, European Journal of Pharmaceutical Sciences, 24, pp. 199-205, 2005.
Koetz, et al., Recovery of Nanoparticles Produced in Phosphatidylcholine-Based Template Phases, Journal of Colloid and Interface Science, 284, pp. 190-198, 2005.

(56) References Cited

OTHER PUBLICATIONS

Wang, Progress in Drying Technology for Nanomaterials, Drying Technology, 23: pp. 7-32, 2005.
Williams et al., Disorder and Dissolution Enhancement: Deposition of Ibuprofen on to Insoluble Polymers, European Journal of Pharmaceutical Sciences, 26, 288-294, 2005.
Yin, et al., Bioavailability Enhancement of a COX-2 Inhibitor, BMS-347070, From A Nanocrystalline Dispersion Prepared by Spray-Drying, Journal of Pharmaceutical Sciences, vol. 94, No. 7, Jul. 2005.
Zhao et al., The Influence of Swelling Capacity of Superdisintegrants in Different pH Media on the Dissolution of Hydrochlorothiazide From Directly Compressed Tablets, AAPS PharmSciTech, 6, (1), Article 19, E120-E126, 2005.
Abdelwahed, et al. Freeze-Drying of Nanoparticles: Formulation, Process and Storage Considerations, Advanced Drug Delivery Reviews, 58, pp. 1688-1713, 2006.
Abdelwahed, et al., Investigation of Nanocapsules Stabilization by Amorphous Excipients During Freeze-Drying and Storage, European Journal of Pharmaceutics and Biopharmaceutics, 63, pp. 87-94, 2006.
Biradar, et al., A Comparative Study of Approaches Used to Improve Solubility of Roxithromycin, Powder Technology, 169, pp. 22-32, 2006.
Huang, et al., Elimination of Metformin—Croscarmellose Sodium Interaction by Competition, International Journal of Pharmaceutics, 311, pp. 33-39, 2006.
Keck, et al., Drug Nanocrystals of Poorly Soluble Drugs Produced by High Pressure Homogenisation, European Journal of Pharmaceutics and Biopharmaceutics, 62, pp. 3-16, 2006.
Layre, et al., Freeze-Drying of Composite Core-Shell Nanoparticles, Drug Development and Industrial Pharmacy, 32, pp. 839-846, 2006.
Moschwitzer, et al., Spray Coated Pellets as Carrier System for Mucoadhesive Drug Nanocrystals, European Journal of Pharmaceutics and Biopharmaceutics, 62, pp. 282-287, 2006.
Tewa-Tagne, et al., Spray-Dried Microparticles Containing Polymeric Nanocapsules: Formulation Aspects, Liquid Phase Interactions and Particles Characteristics, International Journal of Pharmaceutics, 325, pp. 63-74, 2006.
Ahuja, et al., Studies on Dissolution Enhancement and Mathematical Modeling of Drug Release of a Poorly Water-Soluble Drug Using Water-Soluble Carriers, European Journal of Pharmaceutics and Biopharmaceutics, 65, pp. 26-38, 2007.
El-Malah, et al., Fluid Bed Coating: The Utility of Dual Programmable Pumps for Controlled Gradient Drug Deposition on Pellets, International Journal of Pharmaceutics, 337, pp. 361-364, 2007.
Germani, et al., Preparation and Characterization of Porous Alumina-Based Catalyst Coatings in Microchannels, Chemical Engineering Science, 62, pp. 5084-5091, 2007.
Kesisoglou et al., Nanosizing-Oral Formulation Development and Biopharmaceutical Evaluation, Advanced Drug Delivery Reviews, 59, 631-644, 2007.
Tewa-Tagne, Preparation of Redispersible Dry Nanocapsules by Means of Spray-Drying: Development and Characterisation, European Journal of Pharmaceutical Sciences, pp. 124-135, 2007.
Van Eerdenbrugh, et al., Characterization of Physico-Chemical Properties and Pharmaceutical Performance of Sucrose Co-Freeze-Dried solid Nanoparticulate Powders of the Anti-HIV Agent Loviride Prepared by Media Milling, International Journal of Pharmaceutics, 338, pp. 198-206, 2007.
Aburub, et al., A Critical Evaluation of Fasted State Simulating Gastric Fluid (FaSSGF) that Contains Sodium Lauryl Sulfate and Proposal of a Modified Recipe, International Journal of Pharmaceutics, 347, pp. 16-22, 2008.
Basa et al., Production and in vitro Characterization of Solid Dosage Form Incorporating Drug Nanoparticles, Drug Development and Industrial Pharmacy, 34, 1209-1218, 2008.
Chan et al., Size Ratio Effects on Interparticle Interactions and Phase Behavior of Microsphere-Nanoparticle Mixtures, Langmuir, 24, pp. 11399-11405, 2008.
Chaubal, et al., Conversion of Nanosuspensions Into Dry Powders by Spray Drying: A Case Study, Pharmaceutical Research, vol. 25, No. 10, pp. 2302-2308, Oct. 2008.
Choi et al., Effect of Polymer Molecular Weight on Nanocomminution of Poorly Soluble Drug, Drug Delivery. 15, 347-353, 2008.
De Waard, et al., A Novel Bottom-Up Process to Produce Drug Nanocrystals: Controlled Crystallization During Freeze-Drying, Journal of Controlled Release, 128, pp. 179-183, 2008.
Ding, et al., De-agglomeration of Goethite Nano-Particles Using Ultrasonic Comminution Device, Powder Technology, 187, pp. 1-10, 2008.
Gonnissen, et al., Effect of Maltodextrin and Superdisintegrant in Directly Compressible Powder Mixtures Prepared Via Co-Spray Drying, European Journal of Pharmaceutics and Biopharmaceutics, 68, pp. 277-282, 2008.
Lee, et al., Characteristics of Polymers Enabling Nano-Comminution of Water-Insoluble Drugs, International Journal of Pharmaceutics, 355, pp. 328-336, 2008.
Matteucci, et al., Flocculated Amorphous Nanoparticles for Highly Supersaturated Solutions, Pharmaceutical Research, vol. 25, No. 11, pp. 2477-2487, Nov. 2008.
Nokhodchi et al., Preparation of Spherical Crystal Agglomerates of Naproxen Containing Disintegrant for Direct Tablet Making By Spherical Crystallization Technique, AAPS PharmSciTech. 9, No. 1, 54-59, 2008.
Omidian, et al., Swelling Agents and Devices in Oral Drug Delivery, Journal of Drug Delivery Science Technology, 18, 2, pp. 83-93, 2008.
Rozenberg, et al., Polymer-Assisted Fabrication of Nanoparticles and Nanocomposites, Progress in Polymer Science, 33, pp. 40-112, 2008.
Sun et al., Enhanced Dissolution of Silymarin/Polyvinylpyrrolidone Solid Dispersion Pellets Prepared by a One-Step Fluid-Bed Coating Technique, Powder Technology, 182, pp. 72-80, 2008.
Takano, et al., Rate-Limiting Steps of Oral Absorption for Poorly Water-Soluble Drugs in Dogs; Prediction from a Miniscale Dissolution Test and a Physiologically-Based Computer Simulation; Pharmaceutical Research, vol. 25, No. 10, pp. 2334-2344; Oct. 2008.
Tomoda, et al., Preparation and Properties of Inhalable Nanocomposite Particles: Effects of the Temperature at a Spray-Dryer Inlet Upon the Properties of Particles, Colloids and Surfaces B: Biointerfaces, 61, pp. 138-144, 2008.
Van Eerdenbrugh et al., Alternative Matrix Formers for Nanosuspension Solidification: Dissolution Performance and X-Ray Microanalysis as an Evaluation Tool for Powder Dispersion, European Journal of Pharmaceutical Sciences, 35, 344-353, 2008.
Van Eerdenbrugh et al., Drying of Crystalline Drug Nanosuspensions—The Importance of Surface Hydrophobicity on Dissolution Behavior Upon Redispersion, European Journal of Pharmaceutical Sciences, 35, 127-135, 2008.
Vogt, et al., Dissolution Enhancement of Fenofibrate by Micronization, Cogrinding and Spray-Drying: Comparison With Commercial Preparations, European Journal of Pharmaceutics and Biopharmaceutics, 68, pp. 283, 288, 2008.
Vogt, et al., Cogrinding Enhances the Oral Bioavailability of EMD 57033, A Poorly Water Soluble Drug, in Dogs, European Journal of Pharmaceutics and Biopharmaceutics, 68, pp. 338-345, 2008.
Yaremko, et al., Re-Dispersion of Metal Carbonate Powders in Dispersive Media of Various Chemical Nature, Colloids and Surfaces A: Physicochemical Engineering Aspects, 317, pp. 186-193, 2008.
Zhang, et al., Quantitative Measurement of Nanoparticle Halo Formation Around Colloidal Microspheres in Binary Mixtures, Langmuir, 24, pp. 6504-6508, 2008.
Balasumbramanium et al., The Influence of Superdisintegrant Choice on the Rate of Drug Dissolution, Pharm. Tech., 44-49, 2009.
Fan et al., Impact of Polymers on Dissolution Performance of an Amorphous Gelleable Drug From Surface-Coated Beads, European Journal of Pharmaceutical Sciences, 37, pp. 1-10, 2009.

(56) References Cited

OTHER PUBLICATIONS

Gupta, et al., Preparation and Characterization of Superporous Hydrogels as pH-Sensitive Drug Delivery System for Pantoprazole Sodium, Current Drug Delivery, 6, pp. 505-510, 2009.
Iijima, et al., Tuning the Stability of $TiO_2$ Nanoparticles in Various Solvents by Mixed Silane Alkoxides, Journal of Colloid and Interface Science, 337, pp. 61-65, 2009.
Io, et al., Homogeneous Nanoparticles to Enhance the Efficiency, of a Hydrophobic Drug, Antihyperlipidemic Probucol, Characterized by Solid-State NMR, Molecular Pharmaceutics, vol. 7, No. 1, pp. 299-305, 2009.
Jagadish, B., et al., Enhanced Dissolution and Bioavailability of Raloxifene Hydrochloride by Co-Grinding with Different Superdisintegrants, Chem. Pharm. Bull, 58(3) (2010), Published On-Line Dec. 16, 2009.
Nekkanti, et al., Development and Characterization of Solid Oral Dosage Form Incorporating Candesartan Nanoparticles, Pharmaceutical Development and Technology, 14(3), pp. 290,298, 2009.
Ohshima, et al., Freeze-Dried Nifedipine-Lipid Nanoparticles With Long-Term Nano-Dispersion Stability After Reconstitution, International Journal of Pharmaceutics, 377, pp. 180-184, 2009.
Sanganwar, et al., Nano-Mixing of Dipyridamole Drug and Excipient Nanoparticles by Sonication in Liquid $CO_2$, Powder Technology, 196, pp. 36-49, 2009.
Srinarong, P., et al., Strongly Enhanced Dissolution Rate of Fenofibrate Solid Dispersion Tablets by Incorporation of Superdisintegrants, European Journal of Pharmaceutics Biopharmaceutics 73, 154-161, (2009).
Van Eerdenbrugh, et al., Itraconazole/TPGS/Aerosil® 200 Solid Dispersions Characterization, Physical Stability and in vivo Performance, European Journal of Pharmaceutical Sciences, European Journal of Pharmaceutical Sciences, 38, pp. 270-278, 2009.
VanEerdenbrugh,et al., A Screening Study of Surface Stabilization During the Production of Drug Nanocrystals, Journal of Pharmaceutical Sciences, vol. 98, No. 6, June pp. 2091-2103, 2009.
Voinovich et al., Solid State Mechanochemical Simultaneous Activation of the Constituents of the Silybum Marianum Phytocomplex With Crosslinked Polymers, Jouranl of Pharmaceutical Sciences, 98, 215-228, 2009.
Balasubramaniam, et al., Enhanced Dissolution and Bioavailability of Raloxifene Hydrochloride by Co-Grinding With Different Superdisintegrants, Chemical Pharmaceutical Bulleting, 58(3), 293-300, 2010.
Barzegar-Jalali et al., Co-Grinding as an Approach to Enhance Dissolution Rate of A Poorly Water-Soluble Drug (Gliclazide), Powder Technology, 197, 150-158, 2010.
Cerdeira, et al., Miconazole Nanosuspensions: Influence of Formulation Variables on Particle Size Reduction and Physical Stability, International Journal of Pharmaceutics, 396, pp. 210-218, 2010.
Cózar-Bernal, et al., Role of the Electrokinetic Properties on the Stability of Mebendazole Suspensions for Veterinary Applications, International Journal of Pharmaceutics, 393, pp. 161-166, 2010.
Gharsallaoui, et al., Utilisation of Pectin Coating to Enhance Spray-Dry Stability of Pea Protein-Stabilised Oil-in-Water Emulsions, Food Chemistry, 122, pp. 447-454, 2010.
Heng, et al., Pure Drug Naoparticles in Tablets: What are the Dissolution Limitations, Journal of Nanopart Res, 12, pp. 1743-1754, 2010.
Kim et al., Effective Polymeric Dispersants for Vacuum, Convection and Freeze Drying of Drug Nanosuspensions, Int. J. Pharm. 397, 218-224, 2010.
Kho, et al., Effects of Excipient Formulation on the Morphology and Aqueous Re-Dispersibility of Dry-Powder Silica Nano-Aggregates, Colloids and Surfaces A: Physicochemical and Engineering Aspects, 359, pp. 71-81, 2010.
Kho, et al., Aqueous Re-Dispersibility of Spray-Dried Antibhiotic-Loaded Polycaprolactone Nanoparticle Aggregates for Inhaled Anti-Biofilm Therapy, Powder Technology, 203, pp. 432-439, 2010.
Kho, et al., Aqueous Re-Dispersibility Characterization of Spray-Dried Hollow Spherical Silica Nano-Aggregates, Powder Technology, 198, pp. 354-363, 2010.
Liu, et al., Mechanism of Dissolution Enhancement and Bioavailability of Poorly Water Soluble Celecoxib by Preparing Stable Amorphous Nanoparticles, Journal of Pharmacy and Pharmaceutical Sciences, 13(4), pp. 589-606, 2010.
Rao et al., Dissolution Improvement of Simvastatin by Surface Solid Dispersion Technology, Dissolution Technology 6, 27-34, 2010.
Sanchez, et al., Preparation and Spray Drying of $Al_2O_3$-$TiO_2$ Nanoparticle Suspensions to Obtain Nanostructured Coatings by APS, Surface & Coatings Technology, 205, pp. 987-992, 2010.
Timpe, Drug Solubilization Strategies Applying Nanoparticulate Formulation and Solid Dispersion Approaches in Drug Development, Solubility, pp. 12-21, 2010.
Vijaykumar, et al., Development of Oral Tablet Dosage Form Incorporating Drug Nanoparticles, Research Journal of Pharmaceutical, Biological and Chemical Sciences, 1(4), pp. 952-963, 2010.
Zhu, et al., Effect of Ultrafine Grinding on Hydration and Antioxidant Properties of Wheat Bran Dietary Fiber, Food Research International, 43, pp. 943-948, 2010.
Badawi, et al., et al., Formulation and Stability Testing of Itraconazole Crystalline Nanoparticles, AAPS PharmSciTech, 10 pages, 2011.
Bhakay, A., et al., Novel Aspects of Wet Miling for the Production of Microsuspensions and Nanosuspensins of Poorly Water-Soluble Drugs, Drug Development and Industrial Pharmacy 37(8): 963-976 (2011).
Cheow, et al., Spray-Freeze-Drying Production of Thermally Sensitive Polymeric Nanoparticle Aggregates for Inhaled Drug Delivery: Effect of Freeze-Drying Adjuvants, International journal of Pharmaceutics, 404, pp. 289-300, 2011.
Dong, et al., Controlled Antisolvent Precipitation of Spironolactone Nanoparticles by Impingement Mixing, International Journal of Pharmaceutics, 410, pp. 175-179, 2011.
Forny, et al., Wetting, Disintegration and Dissolution of Agglomerated Water Soluble Powders, Powder Technology, 206, pp. 72-78, 2011.
Hashem, et al., Formulation, Characterization, and Clinical Evaluation of Microemulsion Containing Clotrimazole for Topical Delivery, AAPS PharmSciTech, 8 pages, 2011.
Hu, et al., Continuous and Scalable Process for Water-Redispersible Nanoformulation of Poorly Aqueous Soluble APIs by Antisolvent Precipitation and Spray-Drying, International Journal of Pharmaceutics, 404, pp. 198-204, 2011.
Lebhardt et al., Surfactant-Free Redispersible Nanoparticles in Fast-Dissolving Composite Microcarriers for Dry-Powder Inhalation, European Journal of Pharmaceutics Biopharmaceutics 78, 90-96, 2011.
Li, et al., Formation of Bicalutamide Nanodispersion for Dissolution Rate Enhancement, International Journal of Pharmaceutics, 404, pp. 257-263, 2011.
Li, et al, Preparation and invitro/in vivo Evaluation of Revaprazan Hydrochloride Nanosuspension, International Journal of Pharmaceutics, 408, pp. 157-162, 2011.
Meng, et al., Simultaneous Synthesis, Stabilization, and Self-Assembly of Microscale Drug particles in Polymer Films, Journal of Applied Polymer Science, vol. 120, pp. 2082-2089, 2011.
Mohanachandran, et al., Superdisintegrants: An Overview, International Journal of Pharmaceutical Sciences Review and Research, vol. 6, Issue 1, pp. 105-109, 2011.
Niwa, et al., Design of Dry Nanosuspension with Highly Spontaneous Dispersible Characteristics to Develop Solubilized Formulation for Poorly Water-Soluble Drugs, Pharm res, 11 pages, 2011.
Niwa, et al., Universal Wet-Milling Technique to Prepare Oral Nanosuspension Focused on Discovery and Preclinical Animal Studies—Development of Particle Design Method, International Journal of Pharmaceutics, 405, pp. 218-227, 2011.
Rao, et al., Design of Fast Dissolving Tablets of Metoprolol Tartrate Using Novel Co-Processed Superdisintegrants, International Journal of Pharmaceutical Sciences Review and Research, vol. 8, Issue 2, pp. 147-153, 2011.

(56) References Cited

OTHER PUBLICATIONS

Serno, et al., Protein Stabilization by Cyclodextrins in the Liquid and Dried State, Advanced Drug Delivery Reviews, 63, pp. 1086-1106, 2011.
Tozuka, et al., A Novel Application of x-glucosyl Hesperidin for Nanoparticle Formation of Active Pharmaceutical Ingredients by Dry Grinding, European Journal of Pharmaceutics and Biopharmaceutics, 79, pp. 559-565, 2011.
Vialpando, et al., Evaluation of Ordered Mesoporous Silica as a Carrier for Poorly Soluble Drugs: Influence of Pressure on the Structure and Drug Release, Journal of Pharmaceutical Sciences, vol. 100, No. 8, pp. 3411-3420, 2011.
Bhakay, A., et al., Recovery of BCS Class II Drugs Aqueous Dispersion of Core-Shell Type Nanocomposite Particles Produced via Fluidized Bed Coating, Powder Technology 236:231-234 (Jan. 5, 2012).
Bose, Application of Spray Granulation for Conversion of a Nanosuspension into a Dry Powder Form, European Journal of Pharmaceutical Sciences, European Journal of Pharmaceutical Sciences, 47, pp. 35-43, 2012.
Bourezg, et al., Redispersible Lipid Nanoparticles of Spironolactone Obtained by Three Drying Methods, Colloids and Surfaces A: Physicochemical Engineering Aspects, pp. 1-30, 2012.
Chung, et al., Mechanism of Freeze-Drying Drug Nanosuspensions, International Journal of Pharmaceutics, 437, pp. 42-50, 2012.
Hasa, et al., Mechanochemically Induced Disordered Structures of Vincamine: The Different Mediation of Two Cross-Linked Polymers, International Journal of Pharmaceutics, 436, pp. 41-57, 2012.
Ji, et al., Manipulating Microparticle Interactions Using Highly Charged Nanoparticles, Colloids and Surfaces A: Physicochemical and Engineering Aspects, 396, pp. 51-62, 2012.
Mesnier, et al., A Novel Method to Quantify Tablet Disintegration, Powder Technology, 8 pages, 2012.
Pan, et al., Preparation of Superabsorbent Cellulosic Hydrogels, Carbohydrate Polymers, 87, pp. 1410-1418, 2012.
Passerini et al., A New Approach to Enhance Oral Bioavailability of Silybum Marianum Dry extract: Association of Mechanochemical Activation and Spray Congealing, Phytomedicine. 19, 160-168, 2012.
Shi, et al., The Effect of Annealing and Cryoprotectants on the Properties of Vacuum-Freeze Dried Starch Nanoparticles, Carbohydrate Polymers, 88, pp. 1334-1341, 2012.
Zhu, et al., Atomistic Simulations of Aqueous Griseofulvin Crystals in the Presence of Individual and Multiple Additives, Chemical Engineering Science, 72, pp. 218-230, 2012.
Chamsai, Novel Disintegrating Microcrystalline Cellulose Pellets with Improved Drug Dissolution Performance, Powder Technology, 233, pp. 278-285, 2013.
Bhakay et al., Recovery of BCS Class II Drugs During Aqueous Redispersion of Core-Shell Type Nanocomposite Particles Produced Via Fluidized Bed Coating, Powder Technology, 236, 221-234, 2013.
Kollidon—The Original—Setting New Standards in Stability, Purity and Patient Safety, BASF The Chemical Company, 10 pages, no date.
U.S. Appl. No. 13/829,948, filed Mar. 14, 2013, now U.S. Pat. No. 9,452,107.

* cited by examiner

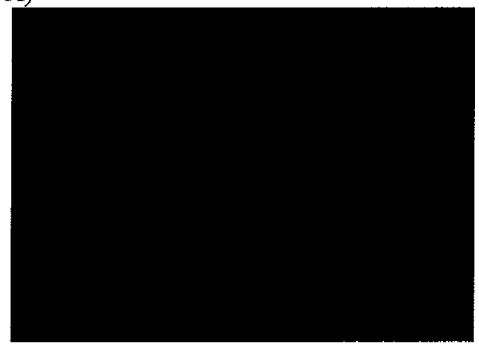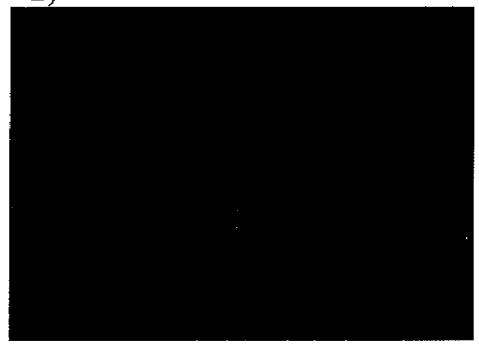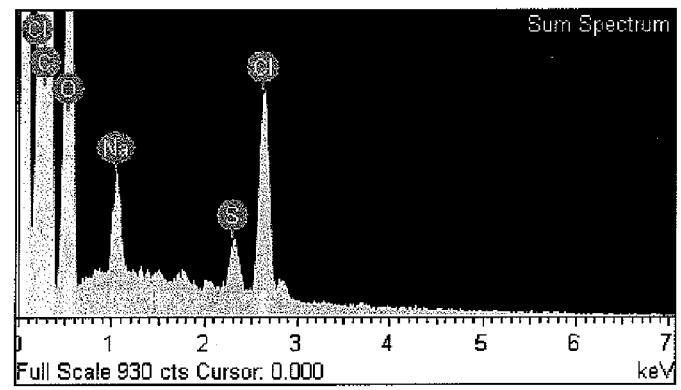
FIGURES 12A-C

METHODS FOR SUPERDISINTEGRANT-BASED COMPOSITE PARTICLES FOR DISPERSION AND DISSOLUTION OF ACTIVE PHARMACEUTICAL AGENTS

CROSS-REFERENCE TO RELATED APPLICATIONS

This application is a divisional application and claims priority to pending U.S. patent application Ser. No. 13/829,948, filed on Mar. 14, 2013. This application also claims the benefit of U.S. Provisional Application Ser. No. 61/625,082 filed Apr. 16, 2012. The entire contents of U.S. patent application Ser. No. 13/829,948 and U.S. Provisional Application Ser. No. 61/625,082 are incorporated herein by reference.

STATEMENT REGARDING FEDERALLY SPONSORED RESEARCH

The present invention was made with government support under Grant Number EEC0540855 awarded by the National Science Foundation. The government has certain rights in this invention.

FIELD OF THE DISCLOSURE

The present disclosure relates to superdisintegrants and, more particularly, to improved systems and methods utilizing superdisintegrant-based composite particles for dispersion and/or dissolution of active pharmaceutical agents.

BACKGROUND OF THE DISCLOSURE

In general, nanoparticles and/or sub-micron (colloidal) particles in the size range of about 10 to about 1000 nm have found use in several applications due to their large surface area among other enhanced engineering properties. These particles are usually produced by wet top-down (size reduction) approaches, or bottom-up (precipitation-based) approaches. Preserving the large surface area and primary size of active nano-particulate agents such as drug substances during wet-phase production and integration into nano-composite micro-particles is generally important.

One issue during the integration step of drying active-loaded nanoparticle suspensions is that nanoparticles typically aggregate and/or agglomerate. This can lead to poor recovery of active (drug) nanoparticles when composite drug-laden micro-particles in various solid dosage forms are re-dispersed in fluids, which in turn can cause loss of surface area and deteriorated active functionality. Incomplete recovery of drug nanoparticles may lead to slow drug dissolution from solid dosage forms and poor drug bioavailability, especially for poorly water-soluble drugs.

In general, the presence of surfactants in formulations has sometimes been found to be important to the recovery of nanoparticles and/or their dissolution. However, in certain applications (e.g., inhalation), surfactants generally cannot be used as they can cause irritation (e.g., to the sensory pulmonary epithelium). In addition, the use of large amounts of surfactants can cause physical instability of drug suspensions through Ostwald ripening and/or agglomeration. Therefore, the development of surfactant-free formulations or formulations with a minimal amount of surfactants is highly desirable.

Dispersants such as sugars (e.g., sucrose, lactose), sugar alcohols (e.g., mannitol, sorbitol), and/or water-soluble polymers (e.g., cellulosic polymer such as HPMC, HPC, PVP, polyvinylalcohol, long chained PEG, etc.) have been added to formulations to enhance drug nanoparticle recovery from the dried nano-composite particles in solid dosage forms. In general, they sometimes allow faster re-dispersion of nanoparticles via enhanced wetting and/or faster matrix dissolution (e.g., wetting/dissolution mechanisms).

In general, particle size engineering is a convenient tool which may be used to control the bioavailability of drugs. Specifically, converting bigger particles into nanoparticles significantly enhances diffusion properties as a result of the large surface area which nanoparticles provide. This knowledge has been used to reduce the particle size of poorly water soluble drugs, via wet stirred media milling (e.g., in such solid dosage forms known as Rapamune©, Emend©, and Tricor©). However, incorporation of nanoparticles into solid dosage forms leads to the loss of their large surface area during drying of nano-suspensions through size growth and/or agglomeration (e.g., forming micro-particles greater than about 1 μm).

The nano-suspensions containing active agents can be dried (e.g., by spray drying, spray freeze drying, freeze drying, etc.), and granulated with or coated on inert excipient particles to convert them into solid dosage forms. During the drying processes, nanoparticles tend to aggregate and form larger particles (sometimes as large as about 1-10 μm particles).

Consequently, the advantages due to the increased surface area via the production of nanoparticles may be lost. These nanoparticle aggregates could be reversible or irreversible depending on the formulation and/or process conditions used during the drying process (see, e.g., Bhakay et al., *Recovery of BCS Class II drugs during aqueous redispersion of core-shell type nanocomposite particles produced via fluidized bed coating*, Powder Technol., 236, 221-234 (2013)). Moreover, the nanoparticles may not be recovered or released from the solid dosage forms fast and/or completely during the re-dispersion/dissolution, either in vivo or in vitro (see, e.g., Kesisoglou et al., *Nanosizing-Oral formulation development and biopharmaceutical evaluation*, Adv. Drug Deliv. Rev. 59, 631-644 (2007)).

In some early works, drug nanoparticles were produced by wet media milling in the presence of hydroxypropyl cellulose (HPC) as a stabilizer, followed by spray and vacuum drying, respectively (see, e.g., Lee J, *Drug nano- and microparticles processed into solid dosage forms: physical properties*, J. Pharm. Sci. 92, 2057-2068 (2003); Choi et al., *Effect of polymer molecular weight on nano-comminution of poorly soluble drug*, Drug Delivery. 15, 347-353 (2008)). The matrix-type nano-composite micro-particles were re-dispersed in water to check the nanoparticle recovery after drying. During the re-dispersion, nano-composite micro-particles released drug nanoparticles over a period of about 25 hours, and nanoparticle recovery was incomplete in some of this work. Also in this work, the micro-particles formed after vacuum drying could not re-disperse into nanoparticles when dispersed in water, even after stirring followed by sonication.

However, drug nanoparticles have been recovered from nano-composite micro-particles obtained from freeze/convective/vacuum drying containing dispersants (e.g., carageenum, gelatin, and alginic acid), as well as HPC as the stabilizer in the re-dispersion tests using sonication (Kim et al., *Effective polymeric dispersants for vacuum, convection and freeze drying of drug nanosuspensions*, Int. J. Pharm. 397, 218-224 (2010)).

Nano-suspension samples have been prepared containing the surfactant D-α-tocopherol polyethylene glycol 1000 succinate (TPGS) as the stabilizer by media milling and spray drying them to form nano-composite micro-particles. (Van Eerdenbrugh et al., *Drying of crystalline drug nanosuspensions—The importance of surface hydrophobicity on dissolution behavior upon redispersion*, Eur. J. Pharm. Sci. 35, 127-135 (2008); Van Eerdenbrugh et al., *Alternative matrix formers for nanosuspension solidification: Dissolution performance and X-ray microanalysis as an evaluation tool for powder dispersion*, Eur. J. Pharm. Sci. 35, 344-353 (2008)). The drug nanoparticles of these poorly water soluble drugs in this case were not recovered in the dissolution testing.

However, they were recovered when additional dispersants like Avicel®, Aerosil®, Fujicalin® and Inutec® were present in the formulation. Some typical dispersants that are added to formulations to preserve the nanoparticle recovery from the dried nano-composite particles are sugars (e.g. sucrose, lactose), sugar alcohols (e.g. mannitol, sorbitol) and water-soluble polymers (e.g. PVP, polyvinylalcohol, long chained PEG).

The ability to recover the drug nanoparticles from nano-composite particles containing polymer hydroxypropylmethyl cellulose (HPMC) and surfactant sodium dodecyl sulfate (SDS) coated on lactose followed by re-dispersion in water has been shown (see, e.g., Basa et al., *Production and in vitro characterization of solid dosage form incorporating drug nanoparticles*, Drug Dev. Ind. Pharm. 34, 1209-1218 (2008)).

Similarly, griseofulvin (GF) nanoparticles have been recovered from the core-shell type nano-composite microparticles containing both HPC and SDS, or SDS alone in the nano-suspension formulation (see, e.g., Bhakay et al., *Recovery of BCS Class II drugs during aqueous redispersion of core-shell type nanocomposite particles produced via fluidized bed coating*, Powder Technol., 236, 221-234 (2013)). However, GF nanoparticles could not be recovered in the absence of SDS, even though mannitol was added as the dispersant.

It has been observed that it can be difficult to reconstitute surfactant free nanoparticles (Jeong et al., *Effect of cryoprotectants on the reconstitution of surfactant-free nanoparticles of poly(DL-lactide-co-glycolide)*, J. Microencapsulation. 22, 593-601 (2005)). From the above examples, surfactants in general have sometimes been able to re-disperse drug nanoparticles after drying.

As noted, surfactants should be either used sparingly due to their potential negative impact on the physical stability of the nano-suspensions, or attempted to be substantially eliminated completely due to their toxicity especially in inhalation applications (Lebhardt et al., *Surfactant free redispersible nanoparticles in fast-dissolving composite microcarriers for dry-powder inhalation*, Eur. J. Pharm. Biopharm. 78, 90-96 (2011); Liversidge et al., *Particle size reduction for improvement of oral bioavailability of hydrophobic drugs: I. Absolute oral bioavailability of nanocrystalline danazol in beagle dogs*, Int. J. Pharm. 125, 91-97 (1995); Liversidge et al., *Surface modified drug nanoparticles*, U.S. Pat. No. 5,145,684). Therefore, there is a need to develop surfactant-free formulations, or formulations with minimal amount of surfactants.

Superdisintegrants ("SDIs") have been used in the past to improve the wettability of drugs by co-grinding in planetary mills and/or ball mills (see, e.g., Voinovich et al., *Solid state mechanochemical simultaneous activation of the constituents of the silybum marianum phytocomplex with cross-linked polymers*, J. Pharm. Sci. 98, 215-228 (2009); Passerini et al., *A new approach to enhance oral bioavailability of silybum marianum dry extract: Association of mechanochemical activation and spray congealing*, Phytomedicine. 19, 160-168 (2012); Martini et al., *Physico-chemical characteristics of steroid-crosslinked polyvinylpyrrolidone coground systems*, Int. J. Pharm. 75, 141-146 (1991); Jalali et al., *Co-grinding as an approach to enhance dissolution rate of a poorly drug (gliclazide)*, Powder Technol. 197, 150-158 (2010)).

They also have been used to make solid dispersions by dispersing the SDI in a drug solution, followed by evaporation of the solvents via lyophilization, vacuum drying, or drying at room temperature (see, e.g., Srinarong et al., *Strongly enhanced dissolution rate of fenofibrate solid dispersion tablets by incorporation of superdisintegrants*, Eur. J. Pharm. Biopharm. 73, 154-161 (2009; Carli et al., *Influence of polymer characteristics on drug loading into crospovidone*, Int. J. Pharm. 33, 115-124 (1986); Williams et al., *Disorder and dissolution enhancement: Deposition of ibuprofen on to insoluble polymers*, Eur. J. Pharm. Sci. 26, 288-294 (2005); Nokhodchi et al., *Preparation of spherical crystal agglomerates of naproxen containing disintegrant for direct tablet making by spherical crystallization technique*, AAPS PharmSciTech. 9, 54-59 (2008); Rao et al., *Dissolution improvement of simvastatin by surface solid dispersion technology*, Dissolution Technol. 6, 27-34 (2010)).

Solid dispersions have been prepared by mixing the drug and SDI in a theta composer, and heating to avoid the use of solvents (see, e.g., Fujii et al., *Preparation, characterization, and tableting of a solid dispersion of indomethacin with crospovidone*, Int. J. Pharm. 293, 145-153 (2005)). Another way of making solid dispersions is to melt the drug and deposit it on a pre-warmed SDI as carrier (Williams et al., 2005). Commercially available SDIs have particles typically in the size ranges of about 5 to about 100 microns.

SDIs are also commonly incorporated in tablets extra-granularly or intra-granularly (or both) for dissolution improvement. The typical mechanisms are that the SDIs absorb water by their swelling and/or wicking actions, which breaks the tablet matrix leading to a disintegration and release of the drug from tablets (Solis et al., *Effect of disintegrants with different hygroscopicity on dissolution of Norfloxacin/Pharmatose DCL 11 tablets*, Int. J. Pharm. 216, 127-135 (2001); Zhao et al., *The influence of swelling capacity of superdisintegrants in different pH media on the dissolution of hydrochlorothiazide from directly compressed tablets*, AAPSPharmSciTech. 6, E120-E126 (2005); Balasumbramanium et al., *The influence of superdisintegrant choice on the rate of drug dissolution*, Pharm. Tech., 44-49 (2009)).

Thus, an interest exists for improved systems and methods utilizing superdisintegrant-based composite particles for dispersion and/or dissolution of active pharmaceutical agents. These and other inefficiencies and opportunities for improvement are addressed and/or overcome by the assemblies, systems and methods of the present disclosure.

SUMMARY OF THE DISCLOSURE

The present disclosure provides advantageous systems and methods utilizing superdisintegrant-based composite particles for dispersion and/or dissolution of active pharmaceutical agents. In exemplary embodiments, the present disclosure utilizes a surfactant-free or near surfactant-free formulation by incorporating a wet milled superdisintegrant (SDI) as a dispersant in the formulation. Stated another way, the present disclosure provides for the preparation of surfactant-free or near surfactant-free formulations (e.g., nano-composite micro-particle formulations) by incorporating a wet-milled superdisintegrant (SDI) as the dispersant in the formulation.

Moreover, the advantageous SDI particles (e.g., colloidal/ultrafine SDI particles) of the present disclosure can also be used to break-up the aggregates (e.g., nanoparticle aggregates) of the active agents (e.g. poorly water-soluble drugs) in the formulations (e.g., micro-particle formulations). The aggregates are typically produced by drying of the drug—SDI suspensions (e.g., nano-suspensions).

In certain embodiments, the present disclosure provides for the production of SDI particles/formulations (e.g., nano/colloidal/ultrafine SDI particles/formulations) by wet milling and/or wet co-grinding the active agents (e.g., poorly water-soluble drugs) along with the SDIs in a wet-stirred media mill in the absence of surfactants or with minimal surfactants present.

The subsequent drying of these suspensions embeds the wet-milled SDI particles along with the active agent (drug). For example, the wet-milled SDI particles along with the active agent may be embedded in the shell of a core-shell (e.g., layered) type formulation (e.g., nano-composite micro-particles formulation), which can be produced by coating on excipients in a fluidized bed dryer/coater or the like. The wet-milled SDI particles along with the active agent may also be embedded in the matrix/formulation of particles (e.g., nano-composite particles) produced by suitable drying techniques (e.g., spray drying, vacuum drying, freeze drying, spray freeze drying oven drying, etc.).

The improved systems and methods of the present disclosure advantageously use SDIs (e.g., colloidal/ultrafine SDIs) as dispersants in formulations (e.g., nano-composite micro-particle formulations), and/or in solid dosage forms/formulations (e.g., formulations containing such composite micro-particles) to achieve fast recovery of active agents (e.g., drug nanoparticles) from solid dosage forms and/or ensuing fast active agent (drug) dissolution.

Embodiments of the present disclosure utilize wet-milled SDIs and/or wet co-ground SDIs along with active agents to form particles/formulations (e.g., nanoparticles or ultrafine particles/formulations) in the presence of stabilizers (e.g., polymeric stabilizers). The suspensions/formulations (e.g., nanoparticle suspensions, nano-suspensions) containing SDI and active agents (e.g., drugs) can be dried for their incorporation in solid dosage forms (e.g., tablets, capsules, strip films, sachets, dry powder inhalers, etc.). In certain embodiments of the present disclosure, SDI particles can also be milled alone into particles (e.g., colloidal/ultrafine particles or nanoparticles) without the active agents in a wet stirred media mill or the like.

The advantageous applications of the SDIs with active agents enable greater recovery of active agent particles (e.g., active agent particles nanoparticles). The present disclosure allows for the quicker/faster and more effective recovery and/or dissolution of active agents (drugs, such as poorly water-soluble drug nanoparticles) from formulations (e.g., nano-composite micro-particles/formulations) via the production of SDI particles (e.g., nano, ultrafine, sub-micron and/or colloidal SDI insoluble dispersant particles), and their incorporation into such formulations (e.g., nano-composite micro-particle formulations).

The present disclosure provides for both SDI particles that are milled alone, or co-ground/co-milled along with active agents (e.g., poorly water-soluble drugs), in a wet-stirred media mill in the presence of stabilizers (e.g., polymeric stabilizers) without the addition of surfactants (or with minimal amount of surfactants) to prepare formulations (e.g., nanoparticle suspensions/formulations) of the SDIs and/or active agents.

A suspension/formulation of co-ground SDI particles with active agents and polymeric stabilizers can be dried by a suitable drying method for the preparation of drug formulations (e.g., nano-composite micro-particle drug formulations). Then, these formulations can be used as powders (e.g., in sachets), or can be incorporated into capsules or tablets, preferably after the addition of generally regarded as safe (GRAS) pharmaceutical excipients (e.g., celluloses, starch, lactose, etc.). The drying methods may include, without limitation, fluidized bed coating/drying/granulation, spray-drying, freeze-drying, vacuum/oven drying, etc.

As such, the systems/methods of the present disclosure lead to the production of surfactant-free (or with minimal surfactants) formulations (e.g., nano-composite micro-particle formulations), which can then be incorporated into a standard solid dosage form or the like via standard pharmaceutical operations (e.g., blending, capsule filling, tableting, etc.).

One advantageous aspect of the present disclosure is the production of colloidal (e.g., typically about 50 to about 500 nm) and/or ultrafine (e.g., typically about 50 to about 5000 nm) superdisintegrant particles by wet milling, either alone or along with active agents (e.g., poorly water-soluble drugs), for the subsequent production/fabrication of fast/quickly-dispersing and/or dissolving formulations (e.g., nano-composite micro-particle formulations).

It has advantageously been demonstrated that the active agents (e.g., drugs, such as poorly water-soluble drug nanoparticles) are recovered quickly and/or more effectively from the formulations (e.g., nano-composite micro-particle formulations containing the wet-milled SDIs) during aqueous re-dispersion under relatively low mechanical agitation/sonication, and significant drug dissolution rate improvements have been achieved in standard dissolution tests. These particles or micro-particles may be incorporated in a standard solid dosage form as mentioned above. It is also noted that the feasibility of wet media milling of the SDI particles alone into particles/nanoparticles or the like has been confirmed by the present disclosure.

The present disclosure provides for a method for fabricating a formulation including providing superdisintegrant (SDI) particles; providing active agent particles; co-wet-milling the SDI particles and the active agent particles to form a mixture of wet-milled SDI particles and active agent particles.

The present disclosure also provides for a method for fabricating a formulation further including the step of drying the mixture of wet-milled SDI particles and active agent particles. The present disclosure also provides for a method for fabricating a formulation further including the step of incorporating the dried mixture into a solid dosage form. The present disclosure also provides for a method for fabricating a formulation wherein at least a portion of the dried mixture is coated on an excipient.

The present disclosure also provides for a method for fabricating a formulation wherein the drying step includes a drying technique selected from the group consisting of fluidized bed drying, spray drying, vacuum drying, freeze drying, spray freeze drying, oven drying, fluidized bed coating and fluidized bed granulation. The present disclosure also provides for a method for fabricating a formulation wherein the mixture further includes a stabilizer. The present disclosure also provides for a method for fabricating a formulation wherein the stabilizer is selected from the group consisting of soluble polymers, hydroxpropylmethyl cellulose, hydroxpropyl cellulose and polyvinylpyrrolidone and combinations thereof.

The present disclosure also provides for a method for fabricating a formulation wherein the mixture of wet-milled SDI particles and active agent particles is a suspension of SDI particles and active agent particles. The present disclosure also provides for a method for fabricating a formulation wherein the suspension contains colloidal and ultrafine SDI particles, and colloidal particles and nanoparticles of active agents. The present disclosure also provides for a method for fabricating a formulation further including the step of drying the suspension to form a nano-composite of SDI and active agent micro-particles.

The present disclosure also provides for a method for fabricating a formulation wherein the active agent particles include particles selected from the group consisting of pharmaceutical active agents, poorly water soluble drugs, diagnostic agents, peptides, proteins, biologic agents and combinations thereof. The present disclosure also provides for a method for fabricating a formulation wherein the SDI particles and active agent particles are co-wet-milled in a wet media mill with milling media; and wherein the milling media has a particle size of about 25 µm to about 4 mm.

The present disclosure also provides for a method for fabricating a formulation wherein the SDI particles and active agent particles are co-wet-milled in size reduction equipment selected from the group consisting of wet stirred media mill, wet ball mill, planetary mill, and milling equipment utilizing a high pressure homogenizer. The present disclosure also provides for a method for fabricating a formulation wherein the SDI particles include particles selected from the group consisting of croscarmellose sodium particles, sodium starch glycolate particles, crosslinked polyvinyl pyrrolidone particles, anionic SDI particles and neutral SDI particles.

The present disclosure also provides for a method for fabricating a formulation wherein the wet-milled SDI particles have a particle size of less than about 5 microns. The present disclosure also provides for a method for fabricating a formulation wherein the mixture of wet-milled SDI particles and active agent particles is a suspension of SDI particles and active agent particles; and further including the step of coating and drying the suspension onto an excipient via a fluidized bed processor to form a nano-composite of SDI and active agent particles on at least a portion of the excipient.

The present disclosure also provides for a method for fabricating a formulation wherein prior to wet-milling the SDI particles and active agent particles, the SDI particles are provided in a suspension at a weight/weight (w/w) % of from about 0.50 w/w % to about 5.0 w/w % with respect to the weight of the water or suspension; and wherein the active agent particles are provided in the suspension at a weight/weight (w/w) % of from about 5.0 w/w % to about 40.0 w/w % with respect to the weight of the water or suspension.

The present disclosure also provides for a method for fabricating a formulation wherein the mixture of wet-milled SDI particles and active agent particles is a suspension of SDI particles and active agent particles; and further including the step of drying the suspension via a spray dryer to form a nano-composite of SDI and active agent particles.

The present disclosure also provides for a method for fabricating colloidal and ultrafine superdisintegrant (SDI) particles including providing SDI particles; wet-milling the SDI particles in a wet media mill to form colloidal and ultrafine SDI particles; wherein the wet-milled SDI particles have a particle size of less than about 5 microns.

The present disclosure also provides for a method for fabricating colloidal and ultrafine SDI particles wherein the wet-milled SDI micro-particles have a particle size of about 50 nm to about 1000 nm. The present disclosure also provides for a method for fabricating colloidal and ultrafine SDI particles further including the step of adding the wet-milled SDI micro-particles to active agent particles. The present disclosure also provides for a method for fabricating colloidal and ultrafine SDI particles wherein the wet-milled SDI micro-particles are mixed with the active agent particles to form a suspension. The present disclosure also provides for a method for fabricating colloidal and ultrafine SDI particles wherein at least a portion of the active agent particles are in powder form.

The present disclosure also provides for a method for fabricating colloidal and ultrafine SDI particles wherein prior to wet-milling the SDI particles, the SDI particles are provided in a suspension at a weight/weight (w/w) % of from about 0.50 w/w % to about 5.0 w/w % with respect to the weight of the water or suspension.

The present disclosure also provides for a method for fabricating colloidal and ultrafine SDI particles further including the steps of: (i) drying the suspension to form a composite of SDI and active agent particles, and (ii) incorporating the dried composite into a solid dosage form.

The present disclosure also provides for a method for fabricating colloidal and ultrafine SDI particles wherein the wet media mill includes milling media, the milling media having a particle size of about 25 µm to about 4 mm. The present disclosure also provides for a method for fabricating colloidal and ultrafine SDI particles further including the step of coating and drying the suspension onto an excipient via a fluidized bed processor to form a composite of SDI and active agent particles on at least a portion of the excipient.

The present disclosure also provides for a method for fabricating a formulation including providing superdisintegrant (SDI) particles and active agent particles in a suspension, the SDI particles provided in the suspension at a weight/weight (w/w) % of from about 0.50 w/w % to about 5.0 w/w % with respect to the weight of the water or suspension; co-wet-milling the SDI particles and the active agent particles in a wet media mill to form a nano-particle suspension of wet-milled SDI particles and active agent particles; drying the nano-particle suspension to form a nano-composite of SDI and active agent micro-particles; incorporating the dried nano-composite into a solid dosage form; wherein the wet-milled SDI particles have a particle size of less than about 5 microns.

Any combination or permutation of embodiments is envisioned. Additional advantageous features, functions and applications of the disclosed assemblies, systems and methods of the present disclosure will be apparent from the description which follows, particularly when read in conjunction with the appended figures. All references listed in this disclosure are hereby incorporated by reference in their entireties.

BRIEF DESCRIPTION OF THE DRAWINGS

Exemplary embodiments of the present disclosure are further described with reference to the appended figures. It is to be noted that the various steps, features and combinations of steps/features described below and illustrated in the figures can be arranged and organized differently to result in embodiments which are still within the spirit and scope of the present disclosure. To assist those of ordinary skill in the art in making and using the disclosed systems, assemblies and methods, reference is made to the appended figures, wherein:

FIGS. 12A-C depict EDX analysis of co-ground FNB and SSG milled sample for detecting sodium (from SSG) and chlorine (from FNB);

DETAILED DESCRIPTION OF DISCLOSURE

Figure 1:
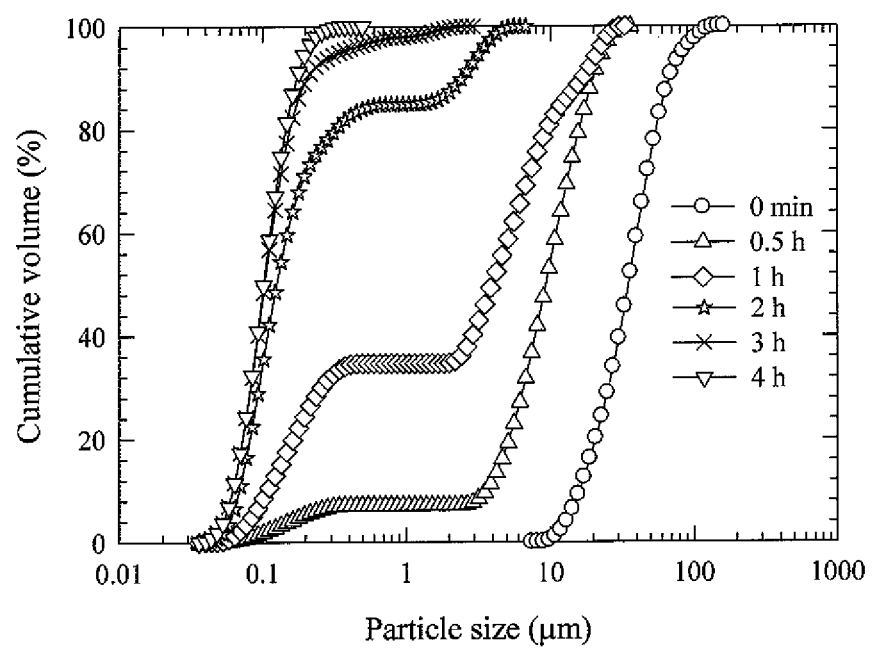
FIG. 1 illustrates the evolution of the cumulative particle size distribution of SSG particles during wet media milling without stabilizers in water.

The following is a detailed description of the disclosure provided to aid those skilled in the art in practicing the present disclosure. Those of ordinary skill in the art may make modifications and variations in the embodiments described herein without departing from the spirit or scope of the present disclosure. Unless otherwise defined, the technical and scientific terms used herein have the same meaning as commonly understood by one of ordinary skill in the art. The terminology used in the description of the disclosure herein is for describing particular embodiments only, and is not intended to be limiting of the disclosure. All publications, patent applications, patents, figures and other references mentioned herein are expressly incorporated by reference in their entireties.

The present disclosure provides improved systems and methods utilizing superdisintegrant-based composite particles for dispersion and/or dissolution of active pharmaceutical agents. In exemplary embodiments, the present disclosure utilizes a surfactant-free or near surfactant-free formulation by incorporating a wet milled SDI as a dispersant in the formulation. Stated another way, the preparation of surfactant-free or substantially surfactant-free formulations (e.g., nano-composite micro-particle formulations) by incorporating a wet-milled superdisintegrant (SDI) as the dispersant in the formulations is provided.

The advantageous SDI particles (e.g., colloidal/ultrafine SDI particles) of the present disclosure can also be used to break-up the aggregates (e.g., nanoparticle aggregates) of the active agents (e.g. poorly water-soluble drugs) in the formulations (e.g., micro-particle formulations).

Current practice provides that commercially available SDI particles are typically in the size ranges of about 5 to about 100 microns, and that colloidal and/or ultrafine SDI particles have not been produced in the art by wet milling. In exemplary embodiments, the present disclosure provides for the co-grinding of SDIs with active agents in the absence of surfactants (or with minimal surfactants), and using the SDIs/composite on the nano/ultrafine/sub-micron/colloidal scale without surfactants (or with minimal surfactants), thereby providing a significant manufacturing, commercial and/or environmental advantage as a result. Moreover, the systems/methods of the present disclosure advantageously lead to the improved or substantially complete recovery of the active agents without (or with minimal) surfactants. According to exemplary systems/methods of the present disclosure, it is noted that colloidal and/or ultrafine SDI particles can now be produced by wet milling.

In certain embodiments, the present disclosure provides for the production of nano/colloidal/ultrafine SDI particles by wet milling, and wet co-grinding of the active agents (e.g., poorly water-soluble drugs) along with the SDIs in a wet stirred media mill in the absence of surfactants or with minimal surfactants present.

As noted, the subsequent drying of these suspensions can embed the wet-milled SDI particles along with the active agent (drug). In certain embodiments, the wet-milled SDI particles along with the active agent may be embedded in the shell of a core-shell (e.g., layered) type formulation (e.g., nano-composite micro-particles formulation), which can be produced by coating on excipients in a fluidized bed dryer/coater or the like. In other embodiments, the wet-milled SDI particles along with the active agent may be embedded in the matrix/formulation of particles (e.g., nano-composite particles) produced by suitable drying techniques (e.g., spray drying, vacuum drying, freeze drying, spray freeze drying, oven drying, etc.).

The systems and methods of the present disclosure advantageously produce SDIs particles (e.g., colloidal/ultrafine SDIs particles) by wet milling and/or co-grinding the SDIs with active agents in a wet stirred media mill or in a wet mill, in general. As such, the systems/methods of the present disclosure can use colloidal/ultrafine SDIs as dispersants in nano-composite micro-particle formulations and solid dosage forms containing such micro-particles to achieve faster/quicker recovery of drug nanoparticles from solid dosage forms and/or ensuring faster/quicker drug dissolution.

Exemplary embodiments utilize wet-milled SDIs and/or wet co-ground SDIs along with active agents to form particles/formulations (e.g., nanoparticles or ultrafine particles/formulations) in the presence of stabilizers (e.g., polymeric stabilizers). The suspensions/formulations (e.g., nanoparticle suspensions) containing SDI and active agents (e.g., drugs) can be dried for their incorporation in solid dosage forms (e.g., tablets, capsules, strip films, sachets, dry powder inhalers, etc.). In certain embodiments, SDI particles can also be milled alone into particles (e.g., colloidal/ultrafine particles or nanoparticles) without the active agents in a wet stirred media mill or the like.

In some embodiments, ultrafine (e.g., about 1 to about 10 microns, preferably less than about 5 microns) and/or colloidal or sub-micron (e.g., less than about 1 micron) particles of superdisintegrants (SDIs) (e.g., croscarmellose sodium, sodium starch glycolate, cross-linked polyvinyl pyrrolidone, etc.) are produced/fabricated via wet milling in suitable milling or size reduction equipment (e.g., wet stirred media milling, wet ball milling, planetary mill, milling equipment utilizing high pressure homogenization, etc.).

SDIs can be co-ground with pharmaceuticals agents (e.g., poorly water soluble drugs) during wet milling in suitable size reduction equipment. The colloidal/ultrafine SDIs can be prepared via wet milling and then mixed with suspensions or powders of pharmaceutical agents including, but not limited to, poorly water-soluble drugs (e.g., BCS Classes II and IV), diagnostic agents, peptides, proteins, biologics, etc. It has been demonstrated that co-grinding SDIs (e.g., wet-milled anionic/neutral SDIs) with drugs (e.g., poorly water-soluble drugs) facilitates the stabilization of the co-ground suspensions.

In general, suspensions containing milled SDIs and pharmaceutical agents (e.g. drugs) can be dried using a suitable drying method known in the art. The present disclosure provides that wet-milled SDIs enable/facilitate the production of surfactant-free nano-composite particle formulations, which thereby allows for the release and efficient recovery and/or dissolution of drug nanoparticles from the formulations. These suspensions/formulations or composite micro-particles can be used as powders, or can be incorporated (e.g., after blending) with commonly used pharmaceutical excipients into a standard solid dosage form such as capsules or tablets through various standard pharmaceutical processes (e.g., granulation, tableting and capsule filling, etc.).

In exemplary embodiments, nano-composite micro-particles produced from fluidized bed coating/drying or spray-drying of co-ground suspensions/formulations of active agents (e.g., poorly water-soluble drugs) and SDIs in a polymer solution exhibited fast release/recovery of drug nanoparticles during aqueous re-dispersion in water. Some drug nanoparticles were recovered within a few minutes even in quiescent water (e.g., without agitation/stirring). Moreover, under paddle stirring, the micro-particles released a considerable fraction of the nanoparticles (16-42%) in about 2 minutes. Importantly, they also exhibited fast/quick drug dissolution (e.g., greater than about 80% drug dissolved within about 10 minutes).

The exemplary co-ground superdisintegrants of the present disclosure are superior to sugars or their alcohols or commonly used neutral polymers as dispersants, and they can replace the surfactants to a significant extent in the production of surfactant-free formulations. As such, the present disclosure advantageously provides for compositions/forms/formulations (e.g., suspensions, solid dosage forms) containing SDI particles (e.g., colloidal and/or ultrafine colloidal SDI particles) produced/fabricated by wet-milling or the like.

In general, SDIs improve tablet dissolution by changing the nature of the drug and/or by promoting the wettability of drugs. SDI's can accomplish this as a result of their swelling or wicking action which breaks the tablet matrix or drug aggregates in the tablet, leading to disintegration of the drug.

Similarly, it is noted that the exemplary SDIs can break nanoparticle aggregates produced during the drying of nano-suspensions. Certain embodiments of the present disclosure utilize ultrafine (e.g., about 1-10 microns) and/or sub-micron (e.g., less than about 1 micron) SDI particles in certain formulations, thus eliminating/reducing the need for other less effective dispersants such as, for example, surfactants, sugars, sugar alcohols, and/or water soluble polymers.

The present disclosure will be further described with respect to the following examples; however, the scope of the disclosure is not limited thereby. The following examples illustrate the advantageous systems and methods of the present disclosure of utilizing SDI-based composite particles for dispersion and/or dissolution of active pharmaceutical agents. As such, the present disclosure advantageously utilizes a surfactant-free or substantially surfactant-free formulation by incorporating a wet milled SDI as a dispersant in the formulation. Stated another way, the preparation of surfactant-free or substantially surfactant-free formulations (e.g., nano-composite micro-particle formulations) by incorporating a wet-milled superdisintegrant (SDI) as the dispersant in the formulations is provided. As noted, the improved SDI particles (e.g., colloidal/ultrafine SDI particles) of the present disclosure can also be used to break-up the aggregates (e.g., nanoparticle aggregates) of the active agents (e.g. poorly water-soluble drugs) in the formulations (e.g., microparticle formulations).

Example 1: Wet Media Milling of a SDI (SSG: Sodium Starch Glycolate)

An SDI, as received sodium starch glycolate (SSG) was sieved in a sieve shaker (Octagon 200) using the US Standard Testing Sieve (ASTM E-11 specification). The sieves had mesh openings of about 106, 63, 45, 38 and about 25 µm. The sieve shaker was operated at an amplitude of about 6 for about 1 hour, and the SSG particles less than about 38 µm were collected and used for media milling.

De-ionized water (about 196 g) was poured into the holding tank and pumped through the milling chamber at a flow rate of about 155 to about 160 ml/min. The percentages weight/weight ("w/w") are expressed with respect to weight of the suspension/mixture. Zirconia beads of about 400 µm were used as the milling media, although the present disclosure is not limited thereto. Rather, it is noted that a variety of milling media may be used with the systems and methods of the present disclosure (e.g., milling media having a particle size of about 25 µm to about 4 mm, such as, for example, crosslinked polystyrene beads, and other suitable milling media or the like).

SSG (about 2% w/w) was added gradually in small amounts within about 12 minutes, while the mill (Netzsch Microcer mill) was running at about 3600 rpm (about 13.2 m/s tip speed). This gradual addition helped prevent lump formation of the SSG particles and prevented clogging of the screen with large, swollen SDI particles. After the addition of SSG, milling was continued for about 3 minutes to ensure proper mixing. A sample was then taken from the holding tank for particle size measurement and was reported as the 0 minute particle size. The suspension/mixture was then milled for about 4 hours.

Figure 2:
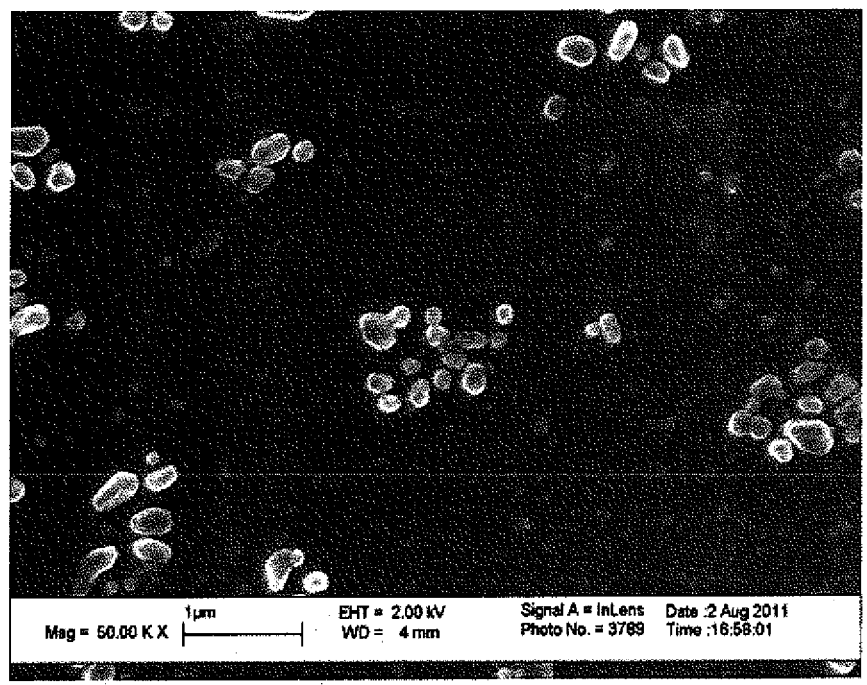
FIG. 2 depicts the SEM image of SSG particles milled for about 4 hours without stabilizers in water.

Samples were taken at 0, 0.5, 1, 2, 3 and 4 hours to investigate the breakage dynamics of SSG in the wet media mill (FIG. 1). The temperature of the mill was kept below about 40° C. with the help of a chiller attached to the mill. An SEM image is shown in FIG. 2. The particle size distributions of the SSG suspensions were measured by laser diffraction via Coulter LS13320 (Beckman Coulter, Miami, Fla., USA) using the Mie theory. The SEM images were taken using scanning electron microscope LEO 1530 SVMP (Carl Zeiss Inc., Peabody, Mass., USA). FIGS. 1-2 present the evolution of the SSG particle size distributions during milling and an SEM image of the milled SSG particles, respectively.

The D90 (e.g., about 90% passing sizes of the cumulative volume distribution) of the 0 minute sample of SSG is about 80 µm, even though its size in the dry form is about 38 µm because it swells in water. The D90, of SSG was reduced to about 200 nm after 4 hour milling in the wet media mill, as can be seen from FIGS. 1-2.

The breakage occurs inside the mill due to frequent bead-bead collisions and fragmentation of the captured particles between the colliding beads. Without being bound by any theory, it is believed that the swelling-induced softening of the SSG particles allowed fast and massive breakage of the SDI particles. Substantially no aggregation of the particles was observed since SSG is an anionic, cross-linked biopolymer that prevents aggregation due to electrostatic repulsion forces. Thus, the feasibility of wet milling the SDI particles down to ultrafine, sub-micron or nano-particles (e.g., less than about 300 nm) has been shown.

Example 2: Wet Co-Grinding of a SDI (CCS: Croscarmellose Sodium) and Two Poorly Water-Soluble Drugs (FNB: Fenofibrate and GF: Griseofulvin) in a Wet Stirred Media Mill The co-grinding of SDI with an active agent (e.g., poorly water-soluble drug), including the mixing of the SDI croscarmellose sodium (CCS) and two BCS II drugs (poorly water soluble drugs) in a wet media mill.

As received CCS particles were sieved using the same conditions as those used for SSG in Example 1 above, and the particles less than about 38 µm were used for the co-grinding experiments. To impart stability to co-ground suspensions/mixtures, a steric stabilizer such as a soluble biopolymer (e.g., hydroxpropylmethyl cellulose (HPMC), hydroxpropyl cellulose (HPC), polyvinylpyrrolidone (PVP), etc.) can be used.

HPMC (HPMC E3 grade, about 1% w/w) was first dissolved in de-ionized water (about 200 g), and Fenofibrate (FNB, a model BCS Class II drug, about 10% w/w) was then added to the stabilizer solution and dispersed for about 30 minutes with a shear mixer. Following the suspension/mixture preparation, the entire batch was poured into the holding tank of the Netzsch mill and pumped through the mill at a speed of about 126 ml/min.

Zirconia beads with a median size of about 400 µm were used as the milling media. Milling speed was set at about 3200 rpm and CCS (about 1% w/w) was added periodically (step-wise) within about 12 minutes to the holding tank to prevent the lumping of CCS particles which may result in clogging of the mill screen (about 200 µm). After the addition of CCS, milling was continued for about 3 minutes to ensure proper mixing. A sample was then taken from the holding tank for particle size measurement and was reported as the 0 minute particle size.

The suspension was then milled for about 2.75 hours at a tip speed of about 11.8 m/s (3200 rpm). Samples were taken at about 0, 0.5, 1, 2 and about 2.75 hours to study the breakage dynamics during co-grinding.

Figure 3:
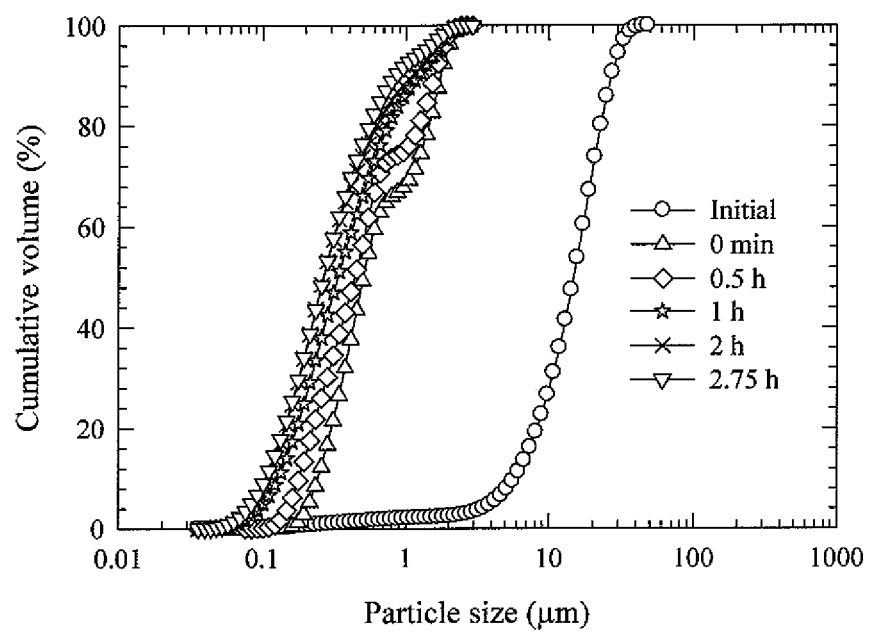
FIG. 3 shows the cumulative particle size distribution of FNB and CCS during co-grinding of FNB (about 10% w/w) and CCS (about 1% w/w) with HPMC E3 (about 1% w/w) as the stabilizer without surfactant in wet media mill.
Figure 4:
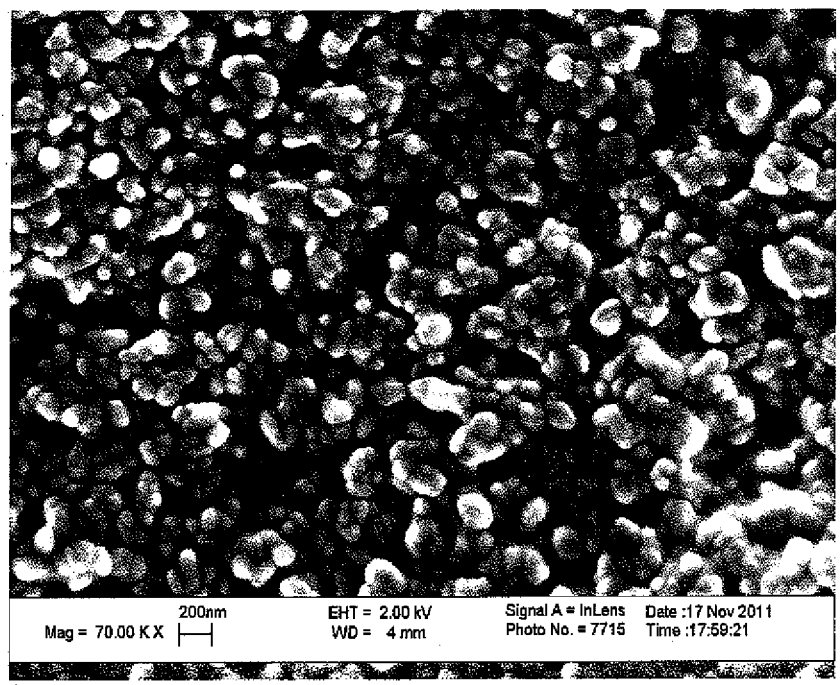
FIG. 4 illustrates the SEM image of co-ground FNB and CCS after milling in the wet media mill for about 2.75 hours in the presence of HPMC E3 without surfactant.

FIG. 3 shows the decrease in particle size of co-ground drug-superdisintegrant (FNB-CCS) as the milling proceeded. The median size (D50) was reduced to about 200 nm after milling for about 2.75 hours, which was also confirmed by the SEM Image (FIG. 4). HPMC reduces the interfacial tension between FNB and water, and acts as a steric stabilizer. CCS is a hydrophilic, anionic SDI which helps to stabilize the suspension further due to electrostatic repulsion.

In another experiment and utilizing the same protocol and milling conditions as noted above, another BCS II drug griseofulvin (GF) at about 10% w/w was co-ground with CCS (about 0.9% w/w) in the presence of HPC (SL grade, about 2.5% w/w) as the stabilizer. This sample was milled for about 80 minutes.

It is noted that the SDI particles may be provided in a suspension at a weight/weight (w/w) % of from about 0.50 w/w % to about 5.0 w/w % with respect to the weight of the water or suspension (preferably at a weight/weight (w/w) % of from about 0.90 w/w % to about 3.0 w/w %), and the active agent particles may be provided in the suspension at a weight/weight (w/w) % of from about 5.0 w/w % to about 40.0 w/w % with respect to the weight of the water or suspension (preferably at a weight/weight (w/w) % of from about 10.0 w/w % to about 30.0 w/w %).

Figure 5:
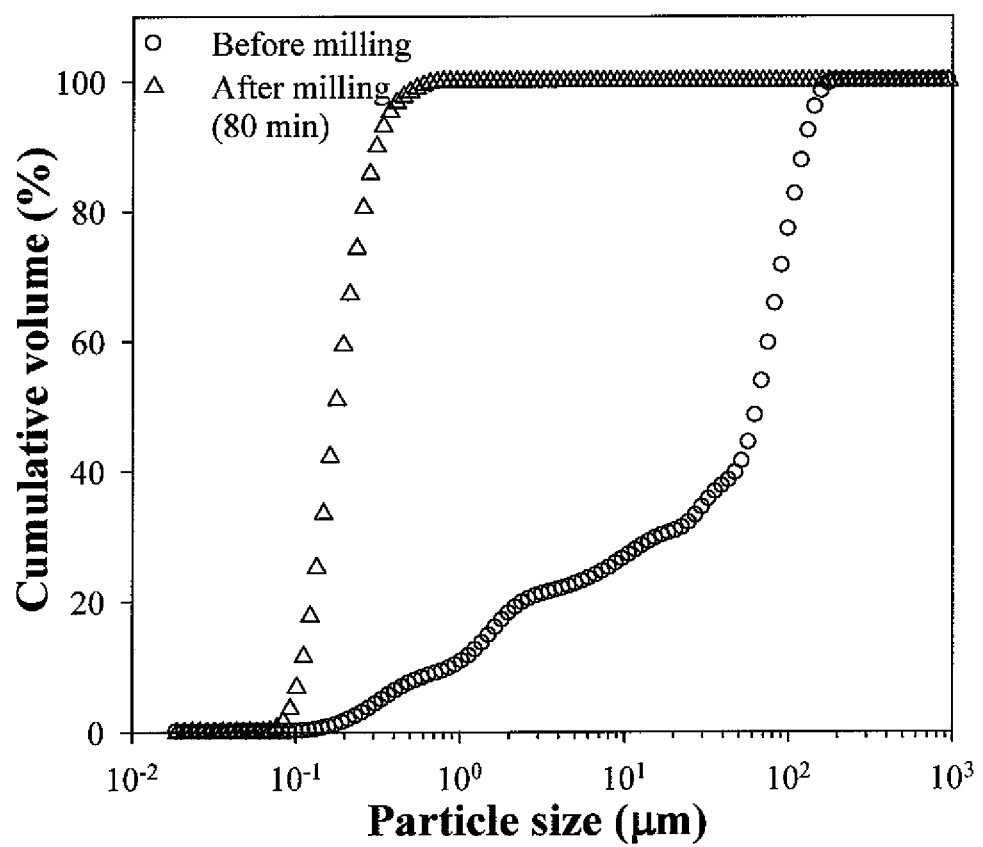
FIG. 5 depicts cumulative particle size distribution of GF and CCS after co-grinding of GF (about 10% w/w) and CCS (about 0.9% w/w) with HPC (about 2.5% w/w) as the stabilizer without surfactant in wet media mill.

The D50 of the other co-ground drug-SDI (GF-CCS) was reduced to about 180 nm (see FIG. 5) after milling for about 80 minutes with HPC as the stabilizer. The milling time of the two drugs varies because of the differences in the breakage strength of the two drugs, e.g., FNB and GF.

Other experiments of the present disclosure include the effective recovery of the active agents after co-grinding with SDIs. One exemplary embodiment for recovering the active agent can be shown using co-ground CCS with GF in nano-composite micro-particles for recovery of GF nano-particles after drying.

The media milling conditions described in the CCS and BCS Class II drugs example described above were used for co-grinding about 0.9% CCS and about 10% GF in about 2.5% HPC solution.

The results from these suspensions were compared to three other formulations: (i) about 2.5% HPC (Hydroxypropyl cellulose, polymer), (ii) about 2.5% HPC with about 0% Mannitol (Mann, sugar alcohol), and (iii) about 2.5% HPC with about 0.5% SDS (sodium dodecyl sulfate, anionic surfactant). The milling conditions used to prepare these suspensions were same as those used in the previous example. All the suspensions were milled for about 80 minutes. It is noted that other surfactants (e.g., polymeric surfactants) may be utilized, preferably in quantities much smaller than their critical micelle concentration, or none at all in surfactant-free formulations.

The suspensions prepared by wet media milling were dried, and then coated on Pharmatose® carrier particles in a conventional bench-top fluidized bed with the top spray configuration. About 100 g Pharmatose® powder with D10, D50, and D90 values of about 58 µm, 116 µm, and 206 µm was charged in the product bowl, and fluidized at an inlet air pressure of about 0.4-0.5 bar.

After the powder was fluidized, the heater and suspension spray were turned on. Approximately 200 g suspension was pumped through a peristaltic pump at a constant speed of about 0.60 ml/min. The suspensions were mixed homogenously with a magnetic stirrer throughout the coating run to prevent sedimentation of particles. The suspensions were atomized through a bi-fluid nozzle with about 0.3 mm nozzle diameter (diameter of the liquid tip) at an atomization air pressure of about 1 bar. The fluidization air temperature was set at about 70° C. The coated powder continued to fluidize and dry for about 10 minutes after the suspension was sprayed. The coated powders were then tested for particle size, and used in re-dispersion and dissolution tests.

About a gram of the nano-composite micro-particles were weighed and dispersed in about 30 ml water for about 2 minutes using sonication. Pharmatose, which forms the core of the coated particles, dissolves in water within about 40 seconds, therefore, the particle size results obtained from Coulter were mainly the sizes of GF and CCS particles and their clusters. Sonication of the sample for about 2 minutes helped/facilitate coated particles to establish good contact with water, and prevented sedimentation of the particles. After dispersing the coated particles in water for about 2 minutes, an aliquot of the sample was taken while the sample was being sonicated and the particle size was measured in LS13320. Dissolution of the coated particles were then determined.

Figure 6:
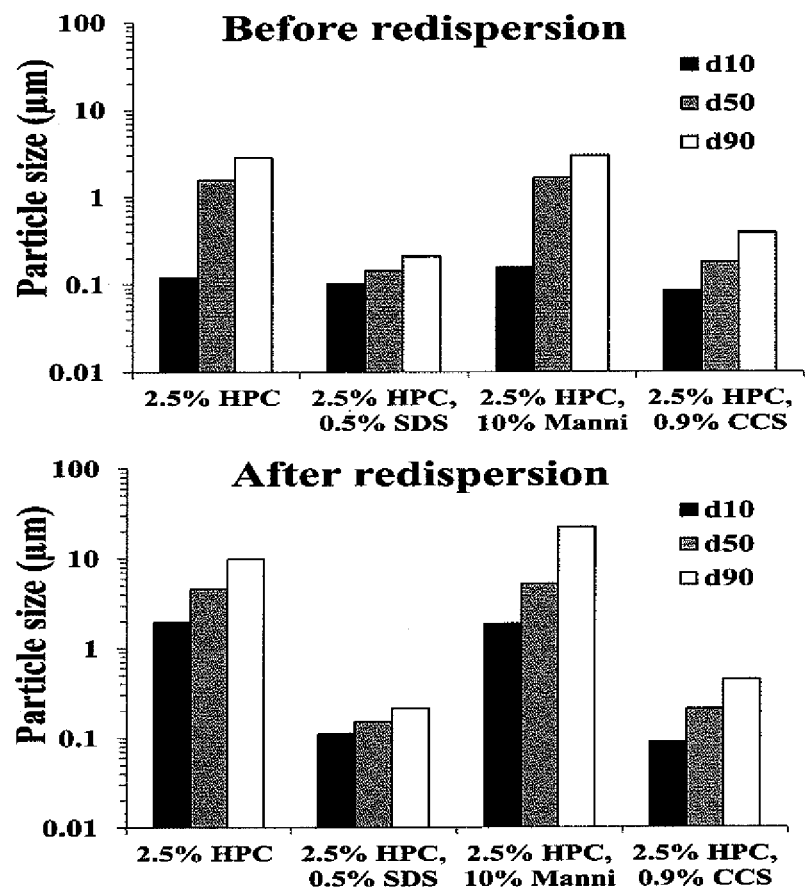
FIG. 6 shows the particle size distribution of milled suspensions before coating and after re-dispersion in water.
Figure 7:
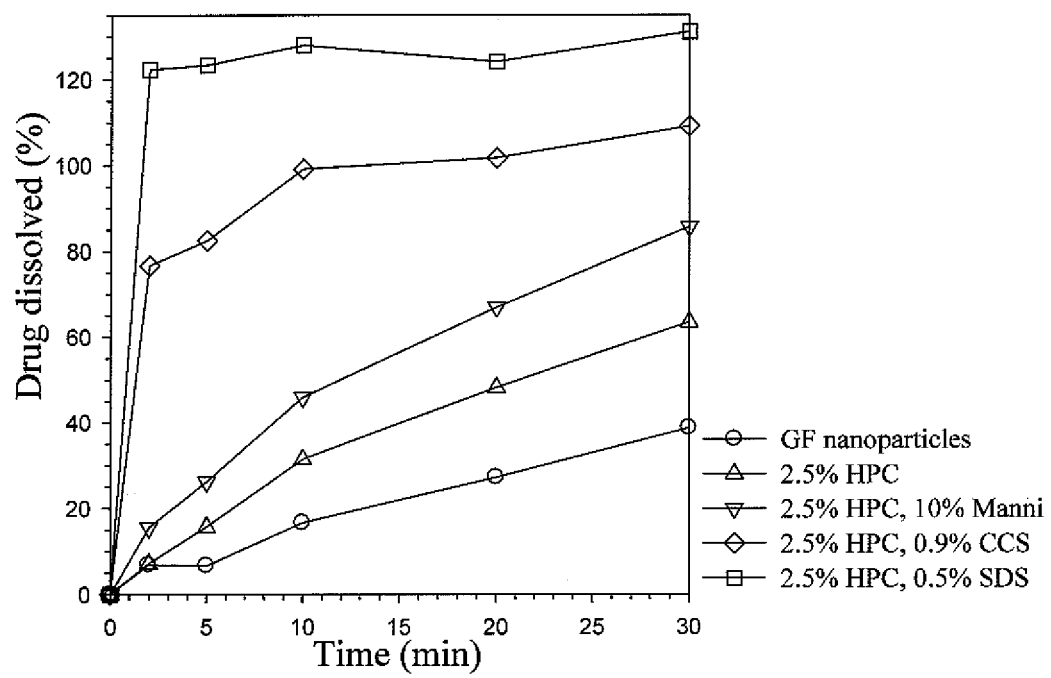
FIG. 7 demonstrates the dissolution profile of GF from nano-composite micro-particles produced with different suspension formulations: about 2.5% HPC, about 2.5% HPC with Mannitol, about 2.5% HPC with CCS, and about 2.5% HPC with SDS.

FIG. 6 shows the particle size distribution of the milled suspensions before coating and after re-dispersion from the nano-composite particles that were obtained from fluidized bed coating/drying. The median size of about 2.5% HPC and about 2.5% HPC with about 10% Mannitol was about 1.6 µm. HPC alone could not disperse the soft aggregates of GF. The median size of GF reduced to about 160 nm in the presence of SDS with HPC.

SDS is an anionic surfactant and reduces the interfacial tension between water and the hydrophobic GF particles, which allows proper wetting of the particles and de-aggregation of the aggregates. Co-grinding of GF and CCS in the presence of HPC also produced nano-suspensions with a median size of about 180 nm.

Figure 8:
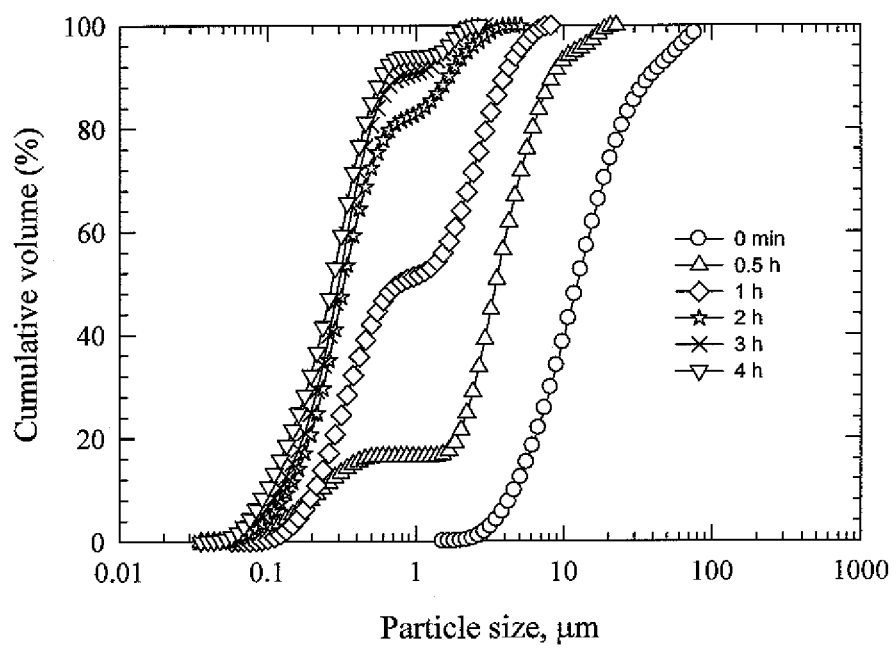
FIG. 8 illustrates the evolution of the cumulative particle size distribution of CP particles during wet media milling without stabilizers in water.
Figure 9:
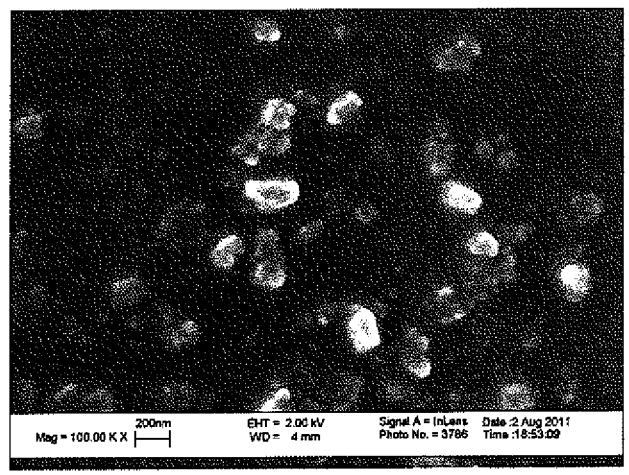
FIG. 9 depicts the SEM image of CP particles milled for about 4 hours without stabilizers in water.

Furthermore, it can be seen that nanoparticles were recovered from the nano-composite particles for formulations containing SDS and CCS. SDS promotes wettability of the nano-composite particles by reducing the interfacial tension. In the absence of SDS, the dissolution action of Mannitol was not enough to disperse the GF aggregates, but it could be dispersed when an insoluble dispersant such as CCS was incorporated in the formulation. CCS is hydrophilic in nature and absorbs water by wicking. It swells on absorption of water, and due to the swelling mechanism it breaks the shell of the nano-composite micro-particles (e.g., coated Pharmatose) and the GF aggregates.

The corresponding improvement in dissolution rate was also observed, as shown in FIG. 7. About 76% of GF was dissolved in about 2 minutes from the GF/HPC/CCS nano-composite particles, whereas only about 15% and about 7% GF was dissolved from GF/HPC/Manni and GF/HPC nano-composite particles, respectively. CCS promotes wettability and recovers GF nanoparticles by its swelling action which leads to increased dissolution rate. However, the highest dissolution rate was observed when SDS was present. These results suggest the feasibility of surfactant-free formulations for improving drug nanoparticles re-dispersion and drug dissolution based on wet milled superdisintegrants.

In addition, the colloidal and/or ultrafine superdisintegrants prepared via wet milling in the present disclosure allow potential minimization of surfactants in pharmaceutical formulations. It is noted that the nano-composite micro-particles (e.g., powders) containing colloidal and/or ultrafine SDIs prepared via wet milling can be incorporated into any standard dosage forms, and the benefits can be extended to different dosage forms.

In certain embodiments, surfactant-free wet milled suspensions of SDIs and active agents were used as-is, while in other embodiments they were dried into composite micro-particles via standard drying operations. Drying the suspensions embeds the SDI along with the active agent in the shell of core shell type nano-composite micro-particles. These dried micro-particles can be directly filled into solid dosage forms including, but not limited to, tablets, capsules, strip films, sachets, dry powder inhalers.

In further embodiments, the micro-particles are compressed into tablets after blending with standard pharmaceutical excipients. Moreover, the micro-particles can be milled via hammer or jet milling into about the 1 to about the 10 microns range for use in inhalation applications or the like.

Example 3: Wet Media Milling of a Superdisintegrant (CP: Crospovidone)

Wet media milling was done with the superdisintegrant alone. As-received Crospovidone (CP) was used in wet media milling. The particle size statistics of the as-received CP was D10-8.14, D50-20.97, and D90-45.70 μm. The milling procedure was similar to that of Example 1 above. The CP loading was about 2% w/w.

The breakage dynamics of CP in the wet media mill is shown in FIG. 8, and an SEM image of the milled particles is shown in FIG. 9. The D90 value of the 0 minute sample is about 41 μm (FIG. 8). It was reduced to about 639 nm after about 4 hours milling in the wet media mill, as can be seen in FIG. 8. Slight aggregation of the CP particles most likely occurred in the suspension because CP is a non-ionic cross-linked polymer and typically does not provide electrostatic repulsion. The primary particle size appears to be less than about 300 nm based on the SEM image (FIG. 9).

It is noted that one can add steric stabilizers like polymers to minimize the aggregation. Despite the aggregation, the feasibility of wet milling the CP particles below about 300 nm, and subsequent preparation of a CP suspension/formulation with greater than about 90% of the particles smaller than about 1000 nm has been shown.

Example 4: Wet Co-Grinding of a Superdisintegrant (SSG: Sodium Starch Glycolate) and a Poorly Water-Soluble Drug (FNB: Fenofibrate) in a Wet Stirred Media Mill SSG and fenofibrate (poorly water soluble drug) were co-ground in a wet media mill. As received SSG particles were sieved and the particles smaller than about 38 μm were used for the co-grinding experiments.

Similar to Example 2, the stability of the co-ground suspensions/mixtures was ensured by using soluble biopolymer Hydroxypropyl methyl cellulose (HPMC-E3). HPMC-E3 (about 1% w/w) was first dissolved in de-ionized water (about 200 g). Fenofibrate (about 10% w/w) was then added to the stabilizer solution and dispersed for about 30 minutes with a shear mixer.

The milling procedure was the same as in Example 2 for CCS and FNB co-ground suspension production. Here, the SSG concentration was about 3% (w/w). Samples were taken at about 0, 1 h, 2 h, and about 2.75 h to study the breakage dynamics during co-grinding. The results are shown in FIGS. 10-12.

Figure 10:
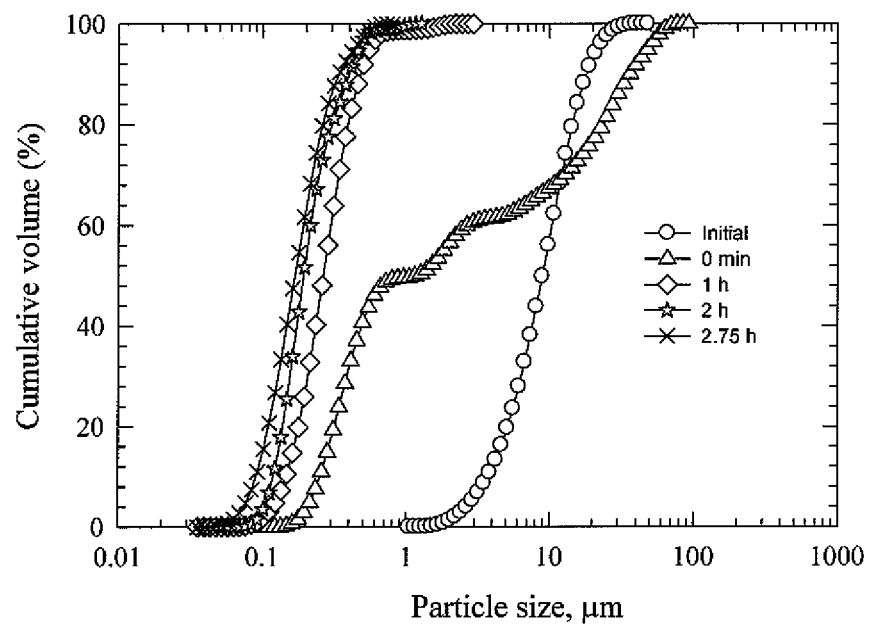
FIG. 10 shows the cumulative particle size distribution of FNB and SSG during co-grinding of FNB (about 10% w/w) and SSG (about 3% w/w) with HPMC-E3 (about 1% w/w) as the stabilizer without surfactant in wet media mill.
Figure 11:
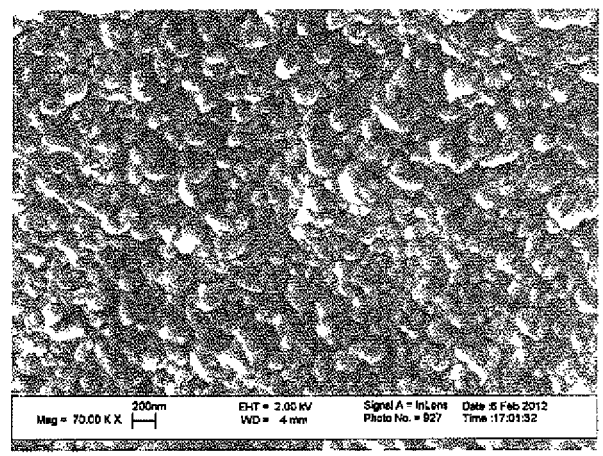
FIG. 11 illustrates the SEM image of co-ground FNB and SSG after milling for about 2.75 hours in the presence of HPMC E3 without surfactant.

FIG. 10 shows the milling dynamics of co-ground drug-superdisintegrant (FNB-SSG). The median size (D50) was reduced to about 184 nm after milling for about 2.75 hours, which was also confirmed by the SEM Image (FIG. 11). HPMC reduces the interfacial tension between FNB and water, and acts as a steric stabilizer. Similar to the CCS, SSG is a hydrophilic, anionic SDI which helps to stabilize the suspensions further due to electrostatic repulsion.

To confirm the presence of nanoparticles of the superdisintegrant in the co-ground suspension sample, an EDX analysis of the dried sample was performed. The EDX analysis is based on the following elements: Na (from SSG) and Cl (from FNB). The EDX map is shown in FIGS. 12A-C. The presence of nano-scale elemental domains originating from nano-milled SSG and FNB can be seen. The EDX analysis proves the presence of nano-particulate SSG in the co-ground suspension. Again, a superdisintegrant (SSG) can be co-ground to nanoparticles along with a BCS Class II (poorly water-soluble) drug and can produce stable nanoparticle suspensions/formulations.

Example 5: Wet Co-Grinding of a Superdisintegrant (CCS: Croscarmellose Sodium) and a Poorly Water-Soluble Drug (GF: Griseofulvin) in a Wet Stirred Media Mill; and Production of Nano-Composite Micro-Particles (NCMPs) Via Fluidized Bed Coating of the Wet-Milled Suspensions onto Pharmatose The formulations of suspensions prepared are listed in Table 1. All percentages (%) refer to w/w with respect to deionized water (about 250 g) when suspensions are considered.

TABLE 1

Formulation of the suspensions and drug (GF) content (with relative standard deviation (RSD)) in nano-composite micro-particles (NCMPs).

| Run No | GF (% w/w)[a] | HPC (% w/w)[a] | SDS (% w/w)[a] | Other additives (% w/w)[a] | Drug content and RSD in NCMPs (% w/w)[a] |
|---|---|---|---|---|---|
| 1 | 10 | 0 | 0 | — | 8.39 (12.91) |
| 2 | 10 | 2.5 | 0 | — | 12.31 (5.77) |
| 3 | 10 | 2.5 | 0 | 10 (Mannitol) | 11.21 (4.94) |
| 4 | 10 | 2.5 | 0.5 | — | 13.61 (4.89) |
| 5 | 10 | 2.5 | 0 | 0.9 (CCS, Unmilled[b]) | 11.91 (2.77) |
| 6 | 10 | 2.5 | 0 | 0.9 (CCS, Milled[c] 60 min) | 12.11 (4.51) |
| 7 | 10 | 2.5 | 0 | 0.9 (CCS, Milled[c] 240 min) | 12.82 (4.34) |
| 8 | 10 | 2.5 | 0 | 0.9 (CCS, Milled[c] + Unmilled)[d] | 12.78 (2.89) |

[a]% w/w is with respect to the weight of de-ionized water for suspensions. It also refers to the weight of GF with respect to the weight of NCMPs.
[b]Unmilled CCS particles are sieved CCS particles that were added to an already milled suspension.
[c]Milled CCS are CCS particles that were co-ground with GF particles.
[d]Contains about 0.45% milled CCS and about 0.45% un-milled CCS.

In Run 1, about 10% GF was dispersed in water for about 30 min using a shear mixer (Fisher Scientific Laboratory stirrer, Catalog no. 14-503, Pittsburgh, Pa., USA) before milling. For Runs 2-8, about 2.5% hydroxypropyl cellulose (HPC, neutral steric stabilizer) was dissolved in water. About 0.5% sodium dodecyl sulfate (SDS, negatively charged electrostatic stabilizer) was added to the HPC solution only in Run 4.

About 10% griseofulvin (GF, poorly water-soluble drug) was then added to the stabilizer solutions (Runs 2-8) and dispersed for about 30 min with the shear mixer. Mannitol (Manni, sugar alcohol) and/or croscarmellose sodium (CCS, superdisintegrant) were used as additional dispersants in Runs 3 and 5-8, respectively. CCS was dry-sieved with a sieve shaker for about 60 min before milling, and a sieve cut off (−550 mesh) was used in Runs 5-8 to minimize the clogging of the mill screen.

Mannitol and sieved CCS particles were added to the already milled suspensions of about 10% GF/about 2.5% HPC in Runs 3 and 5, respectively, using a magnetic stirrer at a speed of about 600 rpm just before coating them onto Pharmatose®. Sieved CCS particles were also added to the co-ground 10% GF/2.5% HPC/0.45% CCS suspension after milling in Run 8 (about 1:1 mass ratio of un-milled CCS to milled CCS). Mannitol has a high solubility in water (about 180 g/L) and dissolves in the GF suspension, whereas CCS is generally insoluble and swells in water.

Following the initial suspension/mixture preparation, about 275 to about 283.5 g suspension was poured into the holding tank of a Netzsch mill (Microcer, Fine particle technology LLC, Exton, Pa., USA) and pumped through the milling chamber at a flow rate of about 126 ml/min.

Zirconia beads with a median size of about 400 μm and a bulk volume of about 50 ml were used as the milling media in Runs 1-5. For Runs 6-8, about a 50/50 v/v mixture of about 400 μm and about 800 μm zirconia beads was used to break the swollen CCS particles.

Figure 13:
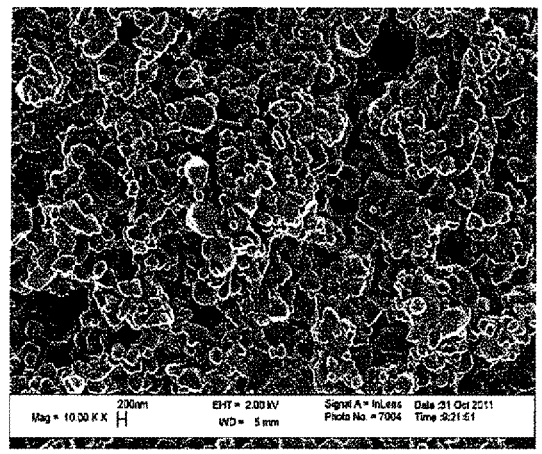
FIG. 13 is a SEM image of GF suspension milled in the absence of stabilizers (Run 1)

CCS powder was added gradually (~0.4 g/min) to the suspension in the holding tank during the initial 6 min of milling because addition of all CCS powder instantaneously typically led to the clogging of the mill screen and shutdown of the process. When added gradually, the CCS particles passed through the milling chamber and fractured while swelling, which helped to minimize the fraction of large swollen particles that can clog the mill. A 200 μm screen was used to retain the beads in the milling chamber.

pension sample (Run 1) shows the presence of primary GF nanoparticles (about 150-600 nm range), even in the absence of stabilizers (FIG. 13).

These findings suggest that micron-sized GF particles were broken down due to frequent bead-bead collisions creating colloidal particles and nanoparticles (defined as <1000 nm per prevalent pharmaceutical engineering terminology), while the particles aggregated in the absence of stabilizers due to the attractive inter-particle forces, such as van der Waals force.

Therefore, the GF suspension was not physically stable in the absence of stabilizers. The median size was reduced to about 1.79 μm after milling in the presence of about 2.5% HPC as a stabilizer. HPC adsorbs on drug particle surface during milling, imparting steric stability and reducing the interfacial tension between GF and water. The particle size of Run 2 suspension stored at about 8° C. did not change significantly 30 h after milling (before re-dispersion). However, the primary GF nanoparticles were in an aggregated state due to the low polymer:drug mass ratio (about 1:4).

TABLE 2

Particle size of the GF and GF-CCS suspensions after milling and before redispersion test (30 h after milling).

| Run No | Formulation (% w/w) | Particle size of suspensions after milling (μm) | | | Particle size of suspensions before redispersion (μm) | | |
|---|---|---|---|---|---|---|---|
| | | D10 | D50 | D90 | D10 | D50 | D90 |
| 1 | No stabilizers | 0.26 ± 0.00 | 2.99 ± 0.02 | 6.13 ± 0.21 | 0.36 ± 0.01 | 4.79 ± 0.02 | 10.65 ± 1.67 |
| 2 | 2.5 HPC | 0.14 ± 0.01 | 1.79 ± 0.05 | 5.35 ± 0.54 | 0.13 ± 0.02 | 1.85 ± 0.10 | 4.24 ± 0.09 |
| 3 | 2.5 HPC, 10 Mannitol[a] | 0.12 ± 0.01 | 1.78 ± 0.12 | 4.33 ± 1.12 | 0.13 ± 0.02 | 1.77 ± 0.09 | 4.52 ± 0.56 |
| 4 | 2.5 HPC, 0.5 SDS | 0.13 ± 0.00 | 0.16 ± 0.00 | 0.22 ± 0.00 | 0.12 ± 0.00 | 0.16 ± 0.00 | 0.21 ± 0.00 |
| 5 | 2.5 HPC, 0.9 CCS (Unmilled)[a] | 0.14 ± 0.02 | 1.85 ± 0.09 | 4.12 ± 0.19 | 0.28 ± 0.02 | 56.18 ± 2.69 | 89.67 ± 4.04 |
| 6 | 2.5 HPC, 0.9 CCS (Milled 60 min) | 0.14 ± 0.01 | 19.52 ± 3.91 | 67.57 ± 2.33 | 0.14 ± 0.00 | 21.79 ± 1.65 | 66.02 ± 5.01 |
| 7 | 2.5 HPC, 0.9 CCS (Milled 240 min) | 0.12 ± 0.00 | 0.16 ± 0.00 | 0.22 ± 0.00 | 0.12 ± 0.00 | 0.16 ± 0.00 | 0.22 ± 0.00 |
| 8 | 2.5 HPC, 0.9 CCS (Milled 120 min + Unmilled) | 0.11 ± 0.02 | 0.16 ± 0.01 | 0.23 ± 0.02 | 0.09 ± 0.00 | 29.7 ± 1.44 | 100.77 ± 2.02 |

[a]The after milling sizes refer to the sizes of GF milled with 2.5% HPC. Sieved CCS and Mannitol were added to the milled suspensions before coating. The sizes of these suspensions are listed under the particle size of suspensions before redispersion.

The suspensions were milled for about 80 min at a tip speed of about 11.8 m/s (3200 rpm) for Runs 1-5, while milling was continued for about 240 min and about 120 min for Runs 7 and 8, respectively. The milling time was purposefully varied in Runs 6-8 to study the impact of particle size of CCS on suspension stability and GF nanoparticle recovery from NCMPs. The temperature inside the milling chamber was maintained at about 32° C. with a chiller (Advantage Engineering, Inc., Greenwood, Ind., USA). Suspension samples were taken from the holding tank for particle size analysis.

The particle size distribution of the milled suspensions was measured by laser diffraction in Coulter LS13320 (Beckman Coulter, Miami, Fla., USA). Suspensions samples were dispersed in about 15 ml of the stabilizer solution and added drop-wise until the polarization intensity differential scattering (PIDS) reached about 40%. The particle size of the GF suspensions was also measured at the end of the fluidized bed coating run, e.g., about 30 hour after milling (about 24 h storage and about 6 h of coating run, also termed as before re-dispersion).

The particle size statistics of as-received GF were D10: 3.9 μm, D50: 16.0 μm and D90: 47.4 μm. Table 2 shows the particle size statistics for GF suspensions in Runs 1-8, after milling and before re-dispersion (about 30 h after milling). In Run 1, GF suspension with a median size of about 2.99 μm was produced. However, the SEM image of this sus- The addition of Mannitol (Run 3) did not alter the aggregation state of the about 10% GF/2.5% HPC suspension (Run 2). Mannitol was added as a dispersant for the downstream processing to aid recovery of the GF nanoparticles. A stable GF nano-suspension was produced when a combination of about 2.5% HPC and about 0.5% SDS was used (Run 4). The median size was about 160 nm and did not change much after 30 h storage. The improved dispersion and stability can be explained by the interactions between HPC and SDS via a complex formation resulting from adsorption of SDS around the hydrophobic sites of HPC.

GF-CCS-HPC suspensions were prepared to study the impact of CCS on milled GF particles. In Run 5, GF was milled with HPC as the stabilizer and sieved particles of CCS were added to this milled suspension via magnetic stirring just before coating the final suspension onto Pharmatose® carrier particles.

The particle sizes of GF suspensions after milling in Runs 2, 3, and 5 (about 10% GF/about 2.5% HPC) indicate that the milling results were fairly reproducible. The median size of Run 5 suspension increased to about 56.18 μm after the addition of CCS before re-dispersion because the CCS particles swelled in water significantly. The dry particle size of CCS, as measured by Rodos/Helos laser diffraction system, was D10: 12.90 μm, D50: 28.55 μm, and D90: 66.09 The particle size increased to D10:13.74 μm, D50: 63.68 μm and D90: 96.28 µm after about 3 h swelling in de-ionized water as measured by Coulter LS13320 with the liquid module.

The increase in particle size of GF/HPC suspension in Run 5 can thus be explained by the fact that the volumetric ratio of swollen CCS particles to GF particles is about 1.7:1 (the mass ratio of dry CCS to GF was about 1:11) and that the volume-based size distribution is governed more by the larger particles than the smaller ones. Hence, the volume-based size distribution of the CCS-GF particles in the suspensions is largely dominated by the larger volume occupied by the swollen CCS particles in the cumulative volume particle size distribution.

In Runs 6 and 7, suspensions containing about 10% GF/about 2.5% HPC were co-ground with CCS particles for about 60 min and about 240 min, respectively, to produce suspensions containing differently sized CCS particles. In Run 8, half of the CCS particles (about 0.45%) were milled with about 10% GF/about 2.5% HPC, and the other half of CCS particles was added after milling in order to have a mixture of un-milled and milled CCS particles. The milling dynamics for the Run 7 suspension are shown in FIG. 14.

The particle size at about 8 min was measured after the gradual addition of CCS was completed in about 6 min. FIG. 14 shows that the median size of the about 2.5% HPC/about 0.9% CCS (Run 7) suspension reduced from about 47.93 µm to about 160 nm after about 240 min of milling. GF breakage dynamics studies have suggested that GF particles were broken down to a median size of <0.2 µm in about 32 min, which did not decrease significantly upon further milling (up to 64 min) under similar milling conditions and formulation (about 2.5% HPC, about 0.5% SDS) used here.

Since a dynamic equilibrium is known to occur within an hour for GF particles, the gradual decrease in the particle size over a period of about 240 min (FIG. 14) can be attributed to slower breakage of the CCS particles as compared with the GF particles. In general, breakage of cross-linked polymers is challenging and wet media milling of CCS in this study achieved the milling objective. CCS, being a cross-linked biopolymer, swells and absorbs water. Swelling induces softening and reduces the tensile strength, which may explain the significant extent of CCS breakage in this study albeit at a slower rate than the GF particles.

Figure 14:
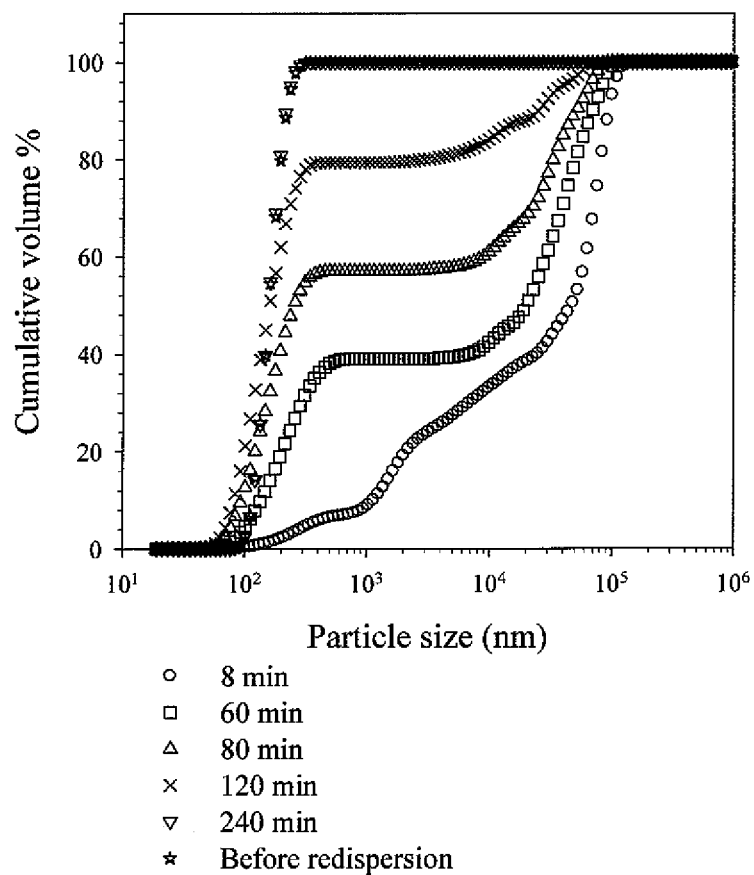
FIG. 14 shows wet stirred media milling of about 10% GF and about 0.9% CCS in the presence of about 2.5% HPC (Run 7) as an evolution of the cumulative particle size distribution over a period of about 240 minutes.
Figure 15:
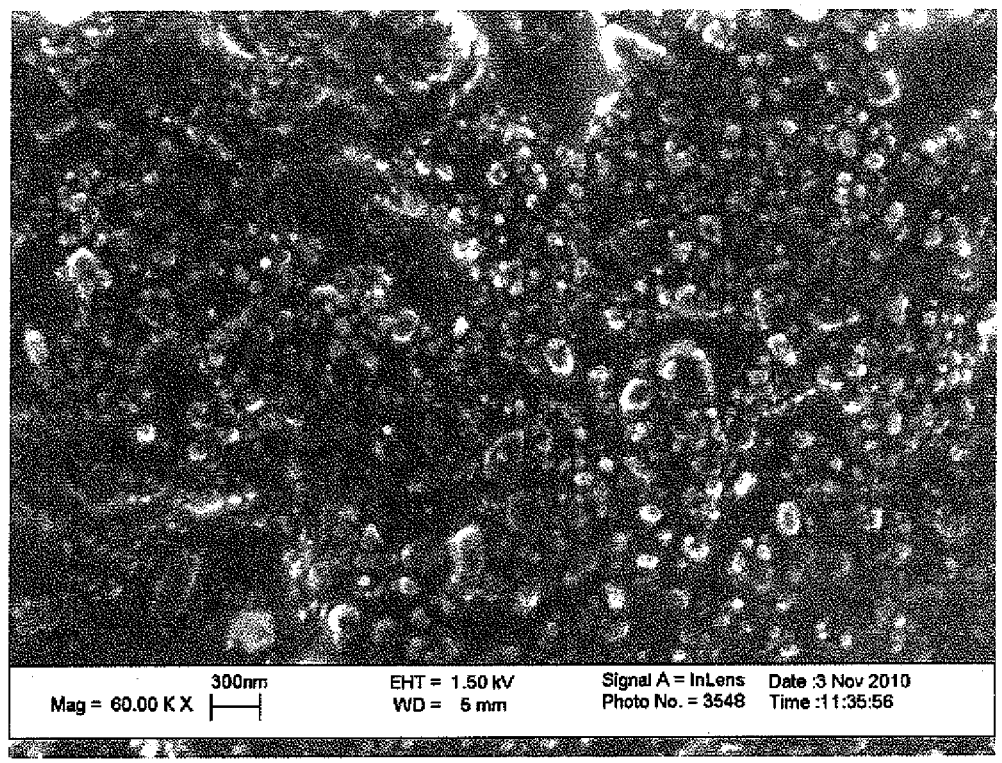
FIG. 15 is a SEM image of the suspension in FIG. 14 after about 240 minutes milling.

FIG. 14 and Table 2 show that the particle size of the Run 7 suspension measured after about 30 h (before re-dispersion) is substantially the same as the particle size obtained after about 240 min of milling, which suggests that the Run 7 suspension was stable. Additional evidence for the presence of GF and CCS nanoparticles in the range of about 50-300 nm in the Run 7 suspension is provided in FIG. 15. For Run 6, the milling of the about 10% GF/about 2.5% HPC/about 0.9% CCS suspension was stopped after about 60 min yielding a mixture of colloidal and larger swollen CCS particles along with GF nanoparticles and their aggregates (median size of about 19.52 µm).

In Run 8, the D50 and D90 particle sizes were about 0.16 µm and about 0.23 µm in the presence of about 0.45% CCS after about 120 min milling, which was similar to that in Run 7 (containing about 0.9% CCS). The median particle size increased to about 29.7 µm before re-dispersion (see Table 2) due to the addition of the remaining 0.45% un-milled CCS particles before the coating of the suspensions (about 30 h after milling).

The D50 and D90 values of the about 10% GF/about 2.5% HPC/about 0.9% CCS suspension (Run 7, Table 2) were about 0.16 µm and about 0.22 µm after about 240 min milling, which are the same as those of the most stable GF suspension, e.g., Run 4 (about 10% GF/about 2.5% HPC/about 0.5% SDS) suspension. Moreover, a comparison of the median sizes of milled suspensions from Run 7 and Run 2 suggests that co-grinding of CCS with GF allowed a finer median size, e.g., about 0.23 µm vs. about 1.79 µm, (about 80 min milling time), respectively.

All these findings point to the enhanced stabilization of GF/HPC suspension in the presence of milled CCS particles. CCS is an anionic superdisintegrant which ionizes into negatively charged croscarmellose ions and sodium cations at pH>2. It is known that colloidal particles (<1000 nm) can be stabilized by charged nanoparticles (about <100 nm) that provide a high electrical charge to the otherwise negligibly charged colloidal particles. It is noted that unlike in the field of colloids, <1000 nm particles are called nanoparticles in the prevalent pharmaceutical terminology. It is also noted that electrostatic action of the milled CCS particles on the stabilization of the GF/HPC suspension is a potential mechanism for the improved stability.

Production of Nano-Composite Micro-Particles ("NCMPs") Via Fluidized Bed Coating of the Wet-Milled Suspensions onto Pharmatose:

The milled suspensions, whose formulations are presented in Table 1, were stored for one day in a refrigerator at about 8° C. to minimize potential growth of particles prior to their coating onto Pharmatose® carrier particles in a conventional bench-top fluidized bed processor (Mini-Glatt, Glatt Air, Ramsey, N.J., USA) with a top spray configuration. About 100 g Pharmatose® powder was charged in the product bowl and fluidized at an inlet air pressure of about 0.4-0.5 bar.

After the powder was fluidized, the heater and suspension spray were turned on. About a 200 g batch of suspension was pumped through a peristaltic pump (Masterflex L/S Cole-Parmer Company, USA) at a rate of about 0.60 ml/min for all runs. The suspensions were mixed with a magnetic stirrer throughout the coating run to prevent sedimentation of the particles. The suspensions were atomized through a bi-fluid nozzle with about 0.3 mm nozzle diameter (diameter of the liquid tip) at an atomization air pressure of about 1 bar. The fluidization air temperature was set at about 70° C. The coated powder continued to fluidize and dry for about 10 min after all the suspension was sprayed for about 6 h. The coated powders were tested for drug assay, particle size, and morphology and were subsequently used in the re-dispersion and dissolution tests.

The suspensions were coated onto Pharmatose® carrier particles in the fluidized bed processor. The particle size statistics of Pharmatose® as measured by Rodos is D10: 58 µm, D50: 116 µm and D90: 206 µm. The median particle size of Pharmatose® increased from about 116 µm to about 120-150 µm due to coating and some agglomeration. The drug content of the nano-composite micro-particles (NC-MPs) was determined by direct assay and is given in Table 1.

In this method, about 100 mg of the dry NCMPs was dissolved in about 20 ml of methanol (solubility of GF in methanol is about 30 mg/ml at about 25° C.) and sonicated for about 30 min to ensure complete dissolution of GF. Pharmatose® particles are generally insoluble in methanol, so they remained suspended. After sonication, they were allowed to sediment, and an aliquot of about 100 µl was taken from the supernatant.

This aliquot was diluted to about 10 ml with methanol. The absorbance of all the samples was measured at the wavelength of about 292 nm by Ultraviolet (UV) spectroscopy in a UV Spectrophotometer (Agilent, Santa Clara, Calif., USA). For each run, six samples from the NCMPs were assayed and the mean drug content along with the relative standard deviation (RSD) was calculated and reported in Table 1.

Figure 16:
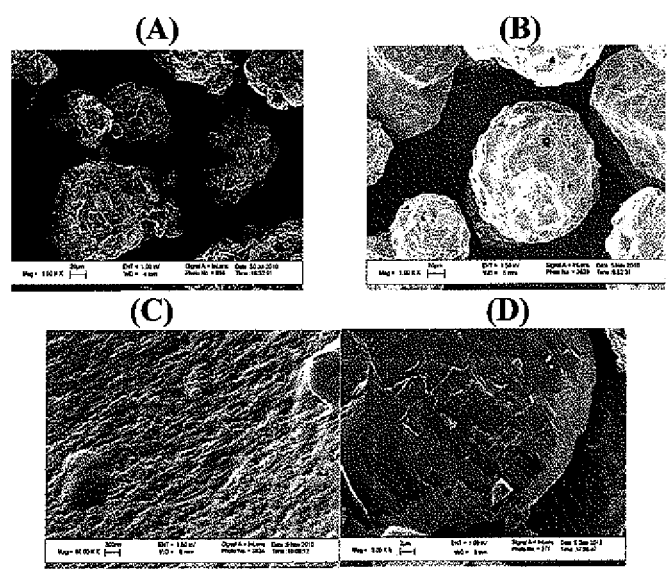
FIGS. 16A-D display SEM images of: (A) uncoated Pharmatose® particles, (B) Pharmatose® particles after coating with about 10% GF/about 2.5% HPC/about 0.5% SDS suspension (Run 4 NCMPs), (C) the surface of a Run 4 NCMP showing embedded GF nanoparticles, and (D) the cross-section of a Run 4 NCMP.

Run 1 shows the lowest GF content of about 8.39% (Table 1). In the absence of HPC, the GF particles could not bind to the surface of Pharmatose® particles strongly and there was preferential loss of GF particles due to attrition during coating. This sample also shows the highest drug content variability. For Runs 2-8, the mean drug content was in the range of 11-14% with less than about 6% RSD for each run. FIG. 16A shows the SEM image of the Pharmatose® particles, and FIGS. 16B-16D show the coated Pharmatose® particles (NCMPs) obtained via drying of the GF/HPC/SDS suspension (Run 4).

From FIGS. 16A and 16B, the surface of as-received and coated Pharmatose® particles appears to be rough with external pores. The lack of smoothness in core Pharmatose® particles led to a non-homogenous coating of the suspensions with a variable thickness of about 2-4 µm in a thin coating layer (FIG. 16D). The coated layer is composed of GF nanoparticles covered by HPC-SDS film and can be clearly seen on the surface of the NCMP in FIG. 16C.

In Runs 2-8, HPC allowed formation of a rough drug-laden coating layer, which embeds and/or partially covers the GF particles on the surface of Pharmatose® particles, thus minimizing the drug loss and assay variability (compare to Run 1 in Table 1). It is noted that both water-soluble (e.g., sugars like Pharmatose® here and sugar alcohols like Mannitol) and insoluble excipients like microcrystalline cellulose, pre-gelatinized starch, etc. can be used as the core material during the fluidized bed coating.

The use of lactose (Pharmatose®) in the current example allows for a thorough and fundamental understanding of GF nanoparticle release from the nano-composite micro-particles because Pharmatose® quickly dissolves during the re-dispersion or dissolution without having confounding effect on the measurement of GF and/or CCS particles. On the other hand, a soluble or insoluble excipient may be used as the core material without loss of generality.

GF nanoparticle recovery during the re-dispersion of the NCMPs was investigated by dispersing about 110-140 mg NCMPs (about 13 mg GF equivalent) prepared above in about 15 ml quiescent, de-ionized water in a vial at room temperature, and video imaging the dispersion. The particle size distribution (PSD) in the supernatant (liquid layer above the sediment) was measured by dynamic light scattering (Beckmann Coulter Delsa Nano C). Different NCMPs are labeled based on their dispersant type/concentration in the respective precursor suspension. Table 3 and FIGS. 17A-D present the PSD statistics and images of the re-dispersions.

TABLE 3

PSD statistics of the supernatants measured via dynamic light scattering (after about 5 min redispersion). For CCS, the abbreviations indicate the following: M: milled, U: unmilled. NM: nanomilled for about 240 min.

| Suspension Formulation (10% GF and various dispersants) | $d_{10}$ (nm) | $d_{50}$ (nm) | $d_{90}$ (nm) |
|---|---|---|---|
| 2.5% HPC | — | — | — |
| 2.5% HPC, 10% Mannitol | — | — | — |
| 2.5% HPC, 0.9% CCS (NM) | 96 | 141 | 260 |
| 2.5% HPC, 0.9% CCS (UM) | 187 | 1417 | 8556 |
| 2.5% HPC, 0.9% CCS (M 60 min) | 124 | 182 | 333 |
| 2.5% HPC, 0.5% SDS | 92 | 129 | 200 |

NCMPs that do not contain CCS or SDS settled down fast, forming a clear supernatant without significant number of particles (below threshold concentration in particle sizing), whereas those with SDS or CCS led to formation of a turbid, milky supernatant with nanoparticles and their clusters. While the descending NCMPs led to induced fluid motion and drag, the drag force could not overcome the gravity; white sediment formed at the bottom of the vials and remained intact after about 30 minutes.

Figure 17:
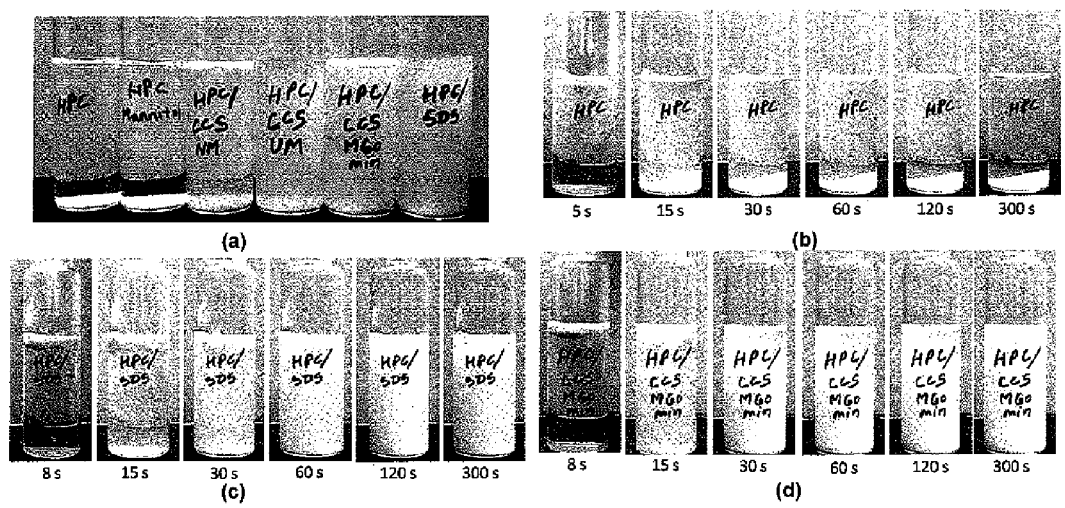
FIGS. 17A-D display video images captured during the re-dispersion of various NCMPs, with different dispersants, in quiescent deionized water: a) 30 min after re-dispersion and evolution of the re-dispersion in the first 300 s for NCMPs with b) 2.5% HPC, c) 2.5% HPC/0.5% SDS, and d) 2.5% HPC/0.9% CCS (M 60 min) in the precursor suspensions. M: milled.

Since nanoparticles and their clusters released were relatively small compared with the NCMPs (Table 3), they were suspended via Brownian motion. It appears that full recovery of all nanoparticles did not occur during re-dispersion in quiescent water. In these videos, it was observed that during their fall, NCMPs with SDS or CCS burst into a cloud of extremely fine particles within about 30 s, which were confirmed to be mainly nanoparticles and their clusters via dynamic light scattering (FIGS. 17C and 17D, Table 3).

Table 3 suggests that except for the NCMPs with un-milled CCS, the supernatants were all colloidal after about 5 min ($d_{90}$<1 µm). Considering the extent/fineness of nanoparticles recovered, a superdisintegrant (about 0.9%) appears to be far more effective than a sugar alcohol (about 10%) at a much lower loading level, and it can potentially replace or minimize use of the surfactant. Moreover, milled superdisintegrant particles can be more effective than un-milled CCS particles for fast release of the GF nanoparticles from NCMPs in quiescent fluids.

Unlike HPC and mannitol which dissolve in water, CCS particles generally do not dissolve, but swell extensively in water and co-exist with the milled GF particles upon re-dispersion of the NCMPs. Hence, in the presence of CCS, a more accurate analysis of GF recovery during re-dispersion should be performed via assaying of the supernatant. In a separate re-dispersion test, about 1 g of the NCMPs was weighed and dispersed in about 30 ml water inside a small beaker for about 2 min via a VWR (VOS 16) paddle stirrer operating at about 240 rpm.

Then, the re-dispersion sample was centrifuged (Becton Dickinson, Compact II centrifuge) for about 10 min at about 3200 rpm to separate the nanoparticles from their aggregates and large, swollen CCS particles. The supernatant obtained was assayed for GF to measure the amount of GF nanoparticles recovered in the re-dispersion test, minimizing any confounding effects due to the CCS particles. To this end, a 40 µl supernatant sample was dissolved in about 10 ml of methanol and UV absorbance of the supernatant was measured at about 292 nm. An aliquot of the supernatant was also used to determine the particle size distribution via laser diffraction and to confirm the feasibility of recovering nanoparticles via centrifugation.

Figure 18:
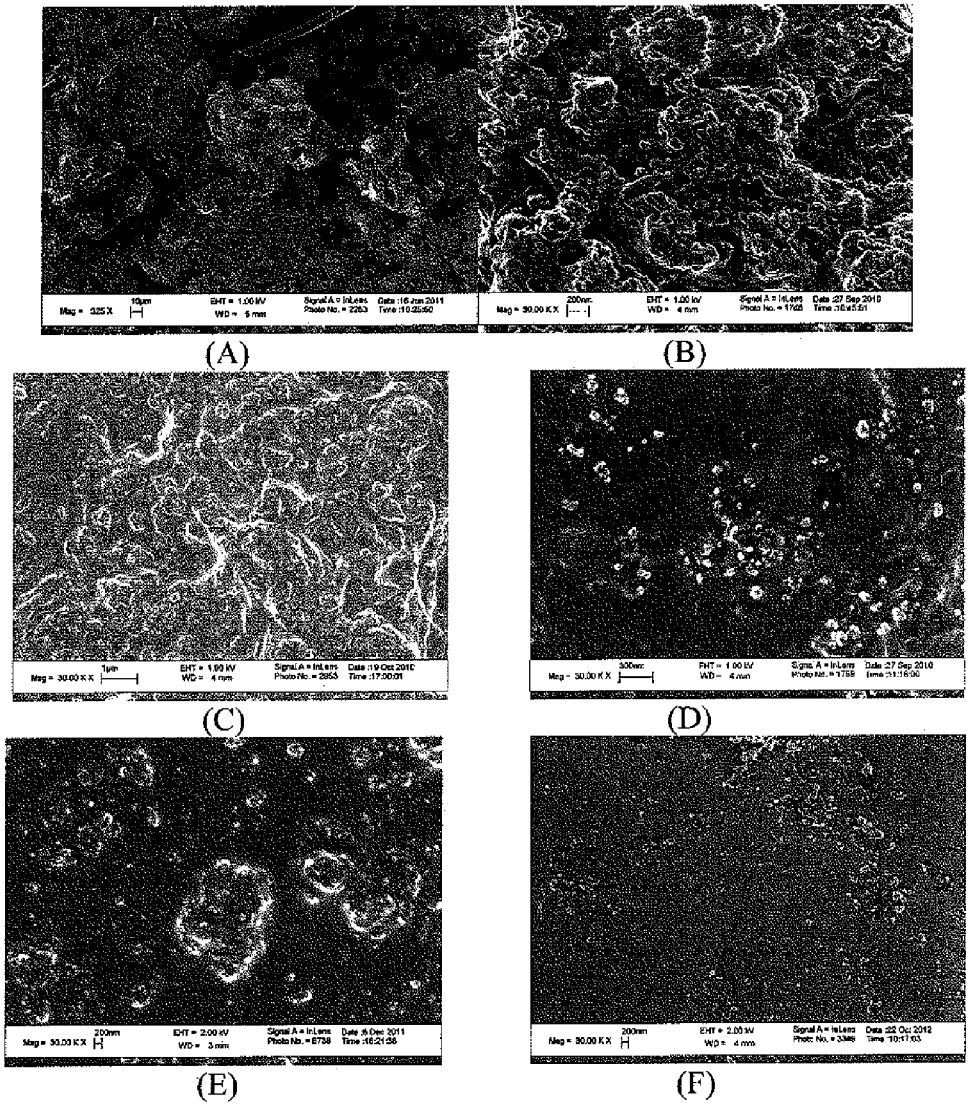
FIGS. 18A-F display SEM images of GF NCMPs after 2 min re-dispersion in water by paddle stirring followed by overnight drying in vacuum—NCMPs containing: (A) GF milled in the absence of stabilizers (Run 1), (B) GF milled with 2.5% HPC (Run 2), (C) GF milled with 2.5% HPC followed by addition of Mannitol (Run 3), (D) GF milled with 2.5% HPC and 0.5% SDS (Run 4), (E) GF milled with 2.5% HPC followed by addition of 0.9% un-milled CCS (Run 5), and (F) GF milled with 2.5% HPC and 0.9% CCS for 60 min (Run 6)

A qualitative assessment of GF nanoparticle recovery from NCMPs after about 2 min re-dispersion with paddle stirring was performed via SEM imaging (FIGS. 18A-F). The GF nanoparticles were not recovered from NCMPs produced without SDS or CCS in Runs 1-3 as shown in FIGS. 18A-18C, which illustrate aggregates of GF nanoparticles.

Discrete GF nanoparticles were recovered from NCMPs containing HPC and SDS (Run 4, FIG. 18D), whereas discrete GF nanoparticles along with some aggregates were re-dispersed from NCMPs containing HPC with un-milled CCS (Run 5, FIG. 18E) and HPC with CCS milled for 60 min (Run 6, FIG. 18F).

Overall, these SEM images suggest that GF nanoparticles were recovered from NCMPs containing SDS or CCS. Extensive SEM imaging of Runs 5 and 6 samples also showed some larger aggregates of GF particles, similar to those observed in FIGS. 18B and 18C, along with the discrete GF nanoparticles. Thus, SEM imaging gives a qualitative and partial picture of the re-dispersion phenomenon.

The particle size of NCMPs after about 2 min re-dispersion with paddle stirring was also measured. The particle sizes before and after re-dispersion in Runs 5-8 refer to sizes of both the GF and CCS particles because CCS is generally insoluble in water. Therefore, information about the GF nanoparticle recovery during the re-dispersion test is partly concealed by the presence of the swollen CCS particles. To overcome this issue, the milled suspension sample was centrifuged to obtain supernatant containing nanoparticles, which was then assayed for GF. The particle sizes of the supernatants, which were obtained from the about 2 min re-dispersion of the NCMPs followed by centrifugation, are reported in Table 4.

HPC formed a film during drying and partially covered the GF nanoparticles. HPC reduces the interfacial tension between GF and water; however, it imparts poorer wettability compared to SDS and dissolves slowly compared to Mannitol or SDS, which led to incomplete recovery of the GF nanoparticles from the GF-HPC agglomerates (clusters) that emanated from the NCMPs during the re-dispersion.

Similarly, addition of Mannitol in Run 3 did not disperse the GF-HPC agglomerates. Mannitol dissolves from the coated layer of the NCMPs creating holes in the surface layer and helps to disperse the GF-HPC agglomerates; however, these agglomerates were not broken further by the dissolution of Mannitol. The inability of Mannitol to release GF nanoparticles completely points to a need for even higher Mannitol to drug ratio (greater than about 1:1). While higher Mannitol to drug ratios may be used for improvement of nanoparticle recovery, a 1:1 ratio is already high and undesirable for a variety of reasons (e.g., high sugar content,

TABLE 4

Percent GF dissolved in 2 min during the USP II dissolution test, T80% of dissolution and percentage GF nanoparticles recovered and their size during the redispersion test.

| Run No | Suspension formulation used in fluidized bed coating | GF dissolved (%) | T80%$^a$ (min) | GF nanoparticles recovered$^b$ (%) | Supernatant particle size$^b$ D10, D50, D90 (μm) |
|---|---|---|---|---|---|
| 1 | 10% GF, No stabilizers | 2.9 ± 1.3 | — | 0.6 ± 0.4 | NM$^c$ |
| 2 | 10% GF, 2.5% HPC | 3.7 ± 1.2 | — | 0.3 ± 0.2 | NM$^c$ |
| 3 | 10% GF, 2.5% HPC, 10% Mannitol | 4.4 ± 3.0 | — | 0.3 ± 0.2 | NM$^c$ |
| 4 | 10% GF, 2.5% HPC, 0.5% SDS | 77.0 ± 0.5 | 5.72 | 89.2 ± 6.9 | 0.123, 0.162, 0.219 |
| 5 | 10% GF, 2.5% HPC, 0.9% CCS (Unmilled) | 33.9 ± 2.4 | 12.62 | 20.6 ± 0.9 | 0.110, 0.154, 0.228 |
| 6 | 10% GF, 2.5% HPC, 0.9% CCS (Milled 60 min) | 58.9 ± 1.2 | 7.55 | 41.8 ± 3.2 | 0.109, 0.161, 0.239 |
| 7 | 10% GF, 2.5% HPC, 0.9% CCS (Milled 240 min) | 27.2 ± 5.1 | 17.68 | 16.2 ± 1.9 | 0.119, 0.157, 0.215 |
| 8 | 10% GF, 2.5% HPC, 0.9% CCS (Milled 120 min + Unmilled) | 48.9 ± 2.4 | 7.85 | 27.8 ± 0.7 | 0.119, 0.159, 0.219 |

$^a$T80%: time required for 80% of GF to dissolve.
$^b$Redispersion: 2 min paddle stirring of the NCMPs in water followed by centrifugation and size analysis of the supernatant.
$^c$NM: Not Measurable. Concentration of the particles was too low for proper detection during sizing in Coulter LS13320.

Table 4 shows that the supernatants of the NCMP formulations with CCS or SDS contained particles mostly <240 nm and that GF nanoparticles were not recovered appreciably in Runs 1-3 in the absence of SDS or CCS in the NCMPs. These findings corroborate the qualitative findings from SEM images in FIGS. 18A-F. The supernatants obtained from Runs 1-3 were clear solutions. The particle concentration was so low that it could not be detected during particle size measurement by laser diffraction for these runs.

However, particles <240 nm were recovered from Runs 4-8 containing SDS or CCS in the NCMPs. Runs 4-8 NCMPs exhibit enhanced GF nanoparticle recovery as compared with Runs 1-3 NCMPs, confirming the successful re-dispersion of the drug nanoparticles in the presence of either SDS or CCS in the coated layer of the NCMPs. However, the formulations in Runs 4-8 cannot be differentiated based on the supernatant particle size distribution because GF nanoparticles in the D10-D90 range of about 110-240 nm (Table 4) were recovered from all runs. On the other hand, these formulations can be rank-ordered based on the percentage GF nanoparticles recovered during the re-dispersion test (Table 4) and the percentage of GF dissolved during the dissolution test (see below).

The GF nanoparticles in Run 1 formed hard aggregates on Pharmatose after drying, which led to only about 0.6% GF recovery from NCMPs (Table 4). Similarly, the soft aggregates of GF in Run 2 suspension with a median size of about 1.79 μm (Table 2) agglomerated and bound together by HPC during drying.

diabetic patients, etc.). Hence, there is a need to find better dispersants that are effective at a smaller dispersant to drug ratio.

GF nanoparticles were completely recovered from the NCMPs when the combination of HPC and SDS was used (Run 4). SDS improved the wettability of the GF-HPC agglomerates, leading to their fast disintegration into nanoparticles or their soft aggregates. The synergistic stabilization effect of HPC/SDS was explained by a complex formation, which resulted in the full recovery and stabilization of the GF nanoparticles. The wetting-dissolution mechanism imparted by HPC and Mannitol (at high concentration about 1:1 with respect to GF) was not sufficient to break the GF-HPC clusters and to recover the GF nanoparticles completely if SDS was not used in the formulation (Runs 2 and 3).

Therefore, a surfactant-free formulation with CCS as a dispersant at low concentration (GF: CCS ratio of about 1:0.09), in addition to HPC, was used in Runs 5 (un-milled CCS), 6 (CCS milled for about 60 min), 7 (CCS milled for about 240 min) and 8 (mixture of un-milled CCS and CCS milled for about 120 min).

The incorporation of CCS in NCMPs promotes swelling-induced breakage of the drug layer of NCMPs and the GF-HPC clusters. CCS is a hydrophilic, water-insoluble superdisintegrant that can promote wettability of the NCMPs. It has a high hydration capacity (about 12.1 g water/g polymer). The swollen CCS particles, which appeared in the milled suspensions, shrunk during the fluidized bed coating process and swelled again in contact with water during the re-dispersion/dissolution of the NCMPs. Swelling of the CCS particles weakens the NCMP layer, causing its faster breakage and facilitating the recovery of the GF nanoparticles from the clusters emanating from the broken layer.

The percentage GF nanoparticles recovered during the re-dispersion test (Runs 5-8) varied depending on the formulation of the NCMPs in the following order: HPC/GF/0.9% CCS milled for 60 min (Run 6) >HPC/GF/0.9% CCS with a 1:1 ratio of 120 min milled and un-milled CCS (Run 8) >HPC/GF/0.9% CCS un-milled (Run 5) >HPC/GF/0.9% CCS milled 240 min (Run 7) (Table 4). Runs 6 and 8 contain a mixture of colloidal and larger milled (Runs 6 and 8)/un-milled (Run 8) CCS particles.

The larger CCS particles are easily accessible by water due to their larger particle size in comparison to the milled CCS particles. In addition, they could exert a higher internal stress upon swelling, leading to more effective weakening of the layered structure of the NCMPs. Therefore, the un-milled CCS particles are expected to be more effective in breaking the surface layer of NCMPs and releasing the GF-HPC agglomerates quickly. Due to their smaller sizes, the agglomerates (about 1-5 µm) may not be broken down effectively by the un-milled CCS particles (D10-D90 size range of 12-66 µm), but by the milled (finer) CCS particles.

On the other hand, the finer CCS particles alone (Run 7) were not very effective in recovering GF nanoparticles because the coated layer did not break quickly in the absence of larger CCS particles. The GF nanoparticle recovery in Runs 5 and 7 containing un-milled CCS and milled (colloidal) CCS, respectively, was not very significant at about 2 min: about 20% and about 16%. These results suggest that some optimum/adjusted milling of CCS along with GF is necessary for improved GF nanoparticle recovery. Indeed, about 60 min GF-CCS co-grinding (Run 6), which caused the lowest extent of CCS particle breakage among all CCS milling cases, imparted the most favorable CCS size characteristics, which led to an improved GF recovery of about 41.8% in about 2 minutes.

A main reason for producing nanoparticles of poorly water-soluble drugs, such as GF, is to improve the dissolution rate of these drugs. Re-dispersion tests can help one to elucidate the drug nanoparticle recovery from NCMPs and to explain the dissolution response. Drug dissolution from all NCMPs (Runs 1-8) and a physical mixture of Run 2 (about 2.5% HPC/about 10% GF) NCMPs with sieved CCS particles in de-ionized water were measured and presented in FIG. 19 and Table 4.

Dissolution tests were carried out in a standard USP II apparatus with about 50 rpm paddle speed. A sample of NCMPs (n=6) containing about 8.9 mg GF were dissolved in about 1000 ml deionized water at about 37° C., and samples taken from the vessel were syringe-filtered (0.1 µm filter) and assayed via UV spectroscopy. Unlike in the re-dispersion test, the use of a large amount of water ensures substantially full solubilization of the drug in this test.

Figure 19:
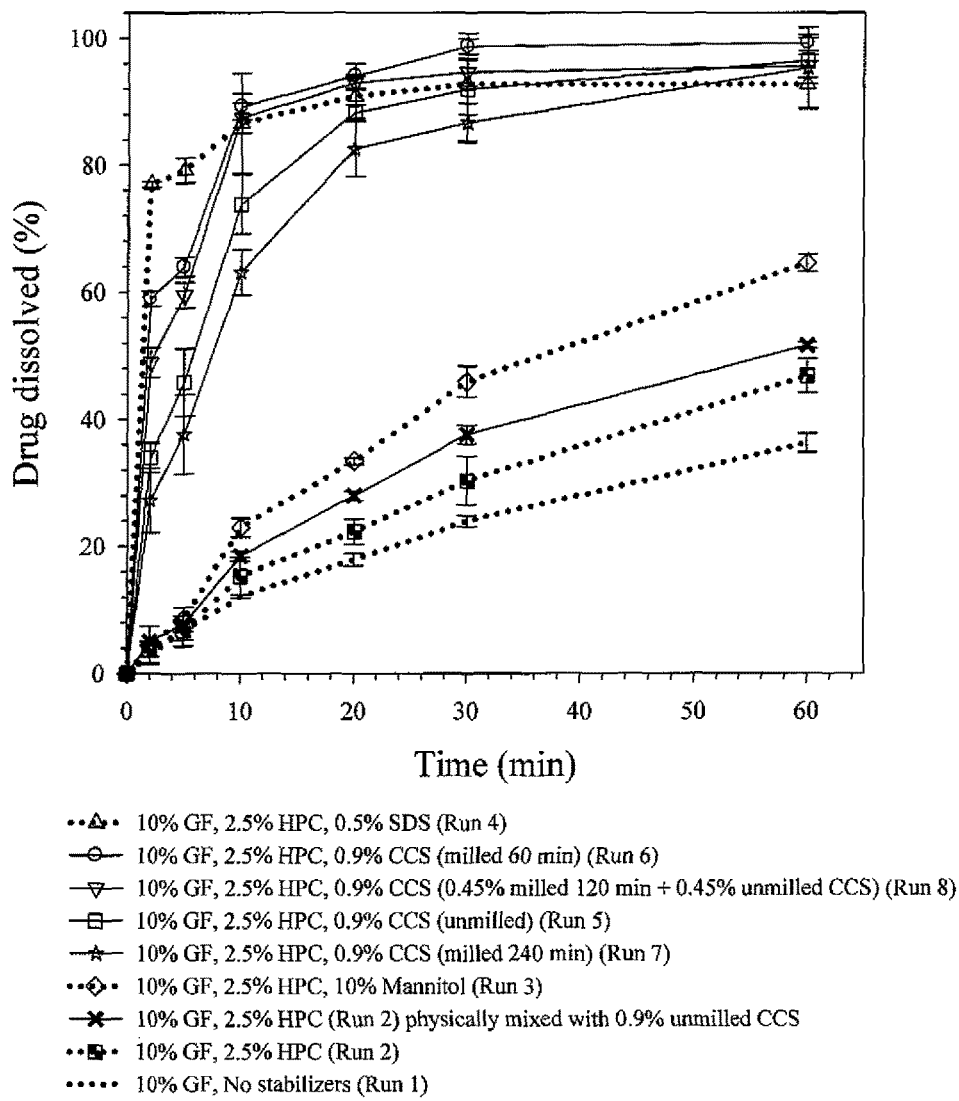
FIG. 19 displays an evolution of GF released and dissolved from the NCMPs during the USP II dissolution test; the NCMPs were prepared using various milled suspensions (Runs 1-8) and from a physical mixture of the un-milled CCS particles with Run 2 NCMPs (about 2.5% HPC/about 10% GF); CCS was present outside the NCMPs in the physical mixture.

The as-received GF particles had extremely slow dissolution in water, with only about 14% of GF being dissolved after about 60 min (result not shown in FIG. 19). The wet media milling of GF particles led to production of aggregates of GF nanoparticles and improved the dissolution rate (Run 1 NCMPs): about 36% in about 60 min (FIG. 19). However, the drug dissolution rate from Run 1 was still low due to poor recovery of the GF nanoparticles from the NCMPs during the dissolution, as also observed in the re-dispersion tests.

The amount of GF dissolved in about 2 min increased slightly from about 2.9% (Run 1) to about 3.7% and about 4.4% when about 2.5% HPC (Run 2) and about 2.5% HPC/10% Mannitol (Run 3) were used in the milled suspensions, respectively. The percentage of GF dissolved from a physical mixture of un-milled CCS particles (CCS outside layered NCMPs) with Run 2 (about 2.5% HPC/about 10% GF) NCMPs was similar to those of Runs 2 and 3 NCMPs: about 5% GF dissolved in about 2 minutes.

As the dissolution progressed, the GF nanoparticles were gradually recovered over a period of time leading to about 47%, 64% and 52% of drug being dissolved from Runs 2, 3 and physical mixture of Run 2 with un-milled CCS particles (CCS outside layered NCMP structure), respectively, in about 60 minutes. Thus, it is concluded that CCS particles outside the NCMP structure typically could not enhance the breakage of the GF-HPC agglomerates and GF nanoparticle recovery/dissolution much.

In Runs 5-8, CCS particles were present in the coated layer of the NCMPs (embedded during fluidized bed coating). The percentage GF dissolved in about 2 min for Runs 5-8 ranged between about 27%-59%, which was about 5-12 times greater than percentage GF dissolution from the physical mixture, where CCS particles were present outside the layered NCMP structure. This finding suggests that it is necessary to incorporate CCS particles into the layered NCMPs for a fast breakage of the coated layer/GF clusters. The un-milled CCS particles were outside of the layered NCMPs in the physical mixture; therefore, they could not exert their swelling-induced breakage action to release GF nanoparticles from their clusters in the NCMPs.

Moreover, T80 (Table 4) in Runs 4-8 containing CCS or SDS is less than about 20 min, which implies a significant improvement in the GF dissolution rate. Dissolution of GF from NCMPs produced in Runs 1-3 and the physical mixture did not reach 80% GF dissolution within about 60 minutes. Therefore, the T80 values for these runs were not reported in Table 4. Also, the dissolution data at about 2 min were analyzed by a paired student t-test, which has been used in literature to compare dissolution profiles. P values of <0.05 were obtained for all runs, except Runs 5 (un-milled CCS) and 7 (milled CCS for about 240 min), thus indicating that the dissolution profiles were statistically different from each other and that the different dispersants had significant effects.

The comparison of the dissolution responses of Runs 5-8 NCMPs, containing a range of CCS particle sizes, suggests the need for an optimal/adjusted CCS particle size for the fastest dissolution rate. Run 6 NCMPs appear to have an optimum/adjusted balance between colloidal and larger milled CCS particles resulting in about 59% dissolution of GF in about 2 minutes. Run 8 NCMPs also consist of milled and un-milled CCS particles and thus have a higher dissolution rate than NCMPs of Runs 5 and 7.

Figure 20:
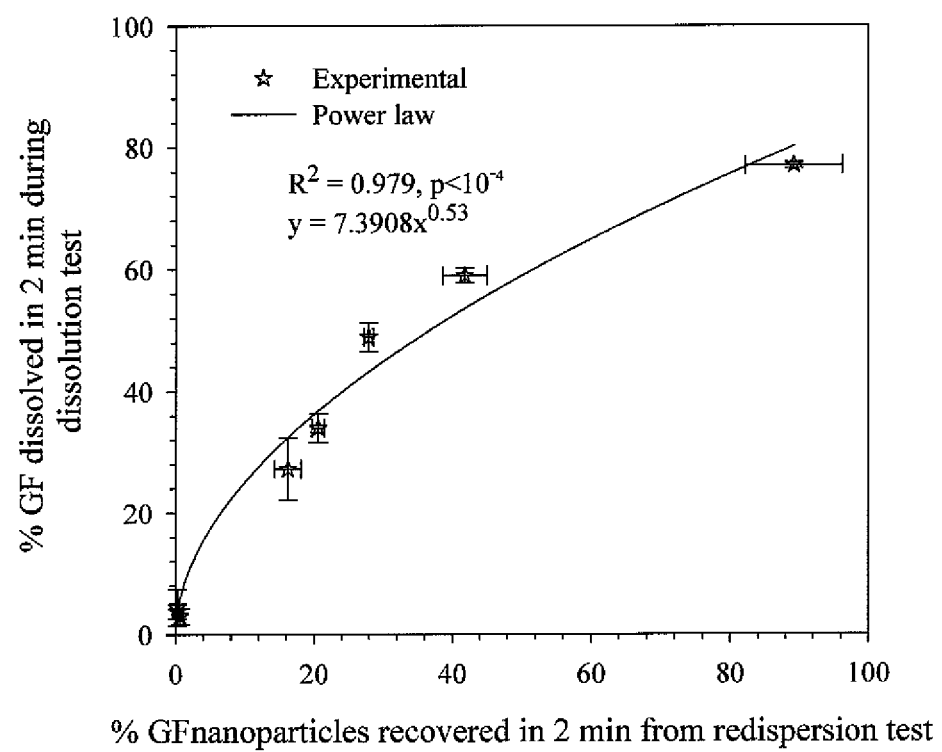
FIG. 20 displays a correlation between percentage of GF dissolved in about 2 min in the USP II dissolution test and percentage of GF nanoparticles recovered in about 2 min during the redispersion test.

Similar observations were made from the re-dispersion test. In fact, a statistically significant empirical correlation, in the form of a simple power-law model (p<0.05 for both the model and its parameters, $R^2$=0.979), was established between the percentage GF dissolved in about 2 minutes during the dissolution test and percentage of the GF nanoparticles recovered during the 2 min re-dispersion test (FIG. 20) for all formulations. Hence, performing a re-dispersion test can be a useful tool for a rough prediction of the dissolution response and allow for rank-ordering of different formulations and focusing on viable formulations during pharmaceutical development. Among all formulations, Run 4, which contains SDS, led to the fastest dissolution of GF. The GF solubility is only slightly increased by SDS below the CMC.

Since the SDS concentration in the dissolution media was estimated to be about 0.044%, which is much less than the CMC of SDS in water at room temperature (about 0.23%), the improved wettability with SDS and resultant improvement in GF nanoparticle recovery can explain the faster dissolution. GF dissolution from Runs 6 and 8 containing milled CCS was also very fast. Overall, CCS and SDS were both found to enhance GF nanoparticle recovery and dissolution through the wetting-dissolution-breakage mechanisms, while CCS also imparts positive effects through the swelling-induced breakage of the NCMPs.

It is also possible to design sophisticated drug formulations with CCS and minimal amount of SDS (below CMC) in drug suspensions. These experiments suggest that SDS can be partially or completely eliminated from drug NCMP formulations without negatively affecting the drug suspension stability and drug nanoparticle recovery during the re-dispersion/dissolution. Hence, the use of colloidal/ultra-fine superdisintegrant particles enable production of surfactant-free, drug (or any other pharmaceutical active agent) nanoparticle-laden, nano-composite micro-particles for fast and effective drug delivery.

Example 6: Incorporation of Co-Ground Superdisintegrant (SSG: Sodium Starch Glycolate) with a Poorly Water-Soluble Drug (GF: Griseofulvin) in Nanocomposite Microparticles (NCMPs) Via Spray-Drying The media milling conditions described in Example 2 were used for co-grinding SSG and GF in the presence of HPC (Hydroxypropyl cellulose, polymer). The formulation was about 10% (w/w) GF, about 2.5% HPC, and about 1% SSG. The suspension was milled for about 79 minutes including the initial 12 minute addition of SSG.

Co-grinding of GF and SSG in the presence of HPC produced a nanoparticle suspension with a median size of about 158 nm. Another suspension without the superdisintegrant (SSG), e.g., a suspension with about 10% GF and about 2.5% HPC, was also produced under the same processing conditions, except that the latter suspension was milled for about 64 minutes.

The nanoparticle suspensions prepared via wet media milling were dried using a spray dryer (4M8-Trix, Procept, Zelzate, Belgium) to produce nano-composite micro-particles. The spray flow setup was co-current. So, the hot air flow and spray of suspension was substantially in the same direction.

The air flow rate and the air temperature was about 0.4 $m^3$/min and about 120° C., respectively. The cyclone separator pressure was maintained at about 55-60 mbar. The suspensions were atomized through a bi-fluid nozzle with about 0.6 mm nozzle diameter (diameter of the liquid tip) at an atomization air pressure of about 2 bars.

The suspensions were pumped at a rate of about 1.3-1.5 g/min using a pump (Make-it-EZ, Creates, Zelzate, Belgium). The suspension was mixed homogenously with a magnetic stirrer throughout the spraying run to prevent sedimentation of the particles. The spray-dried powders were then tested for particle size and used in the dissolution tests.

The dissolution procedure was similar to that of Example 5. The samples were taken out manually at about 1, 5, 10, 20, 30 and about 60 minutes.

Figure 21:
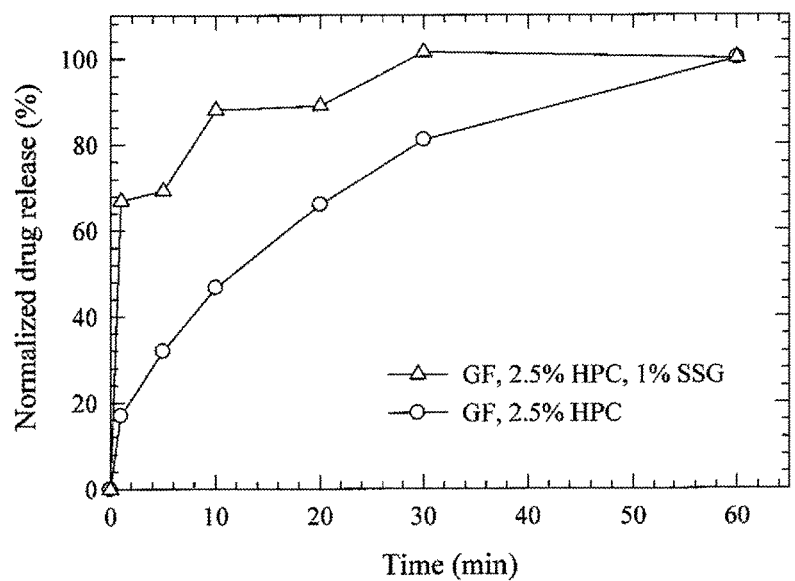
FIG. 21 illustrates the dissolution profile (dissolution medium—water) of GF from spray dried nano-composite micro-particles produced with different suspension formulations: about 2.5% HPC, and about 2.5% HPC/about 1% SSG.

FIG. 21 shows the dissolution rate improvement by the colloidal SSG particles in the nano-composite micro-particles produced by spray-drying. About 88% of GF was dissolved in about 10 minutes from the GF/HPC/SSG nano-composite particles, whereas only about 47% GF was dissolved from GF/HPC nano-composite particles.

SSG is an anionic superdisintegrant and hydrophilic in nature. SSG promotes wettability and recovers GF nanoparticles by its swelling action, which leads to increased dissolution rate. Furthermore, similar to colloidal CCS, colloidal SSG swells on absorption of water, and due to the swelling mechanism it breaks the GF aggregates. Thus, SSG can be used to improve dissolution rate and bioavailability of poorly water-soluble drugs such as GF without surfactants (e.g., substantially surfactant-free formulations) or with minimal amount of surfactants. Such results display the feasibility of surfactant-free drug formulation based on wet-milled superdisintegrants.

As seen in certain embodiments, the surfactant-free wet milled suspensions of superdisintegrants and active agents can be used as suspensions, or alternatively can be dried into composite micro-particles via standard drying operations. These micro-particles can be either directly filled into capsules, sachets, etc., or can be compressed into tablets or the like after blending with standard pharmaceutical excipients. In further embodiments, the micro-particles can be further milled via hammer or jet milling into about the 1-10 micron range for use in inhalation applications or the like. The present disclosure covers applications involving the production/fabrication, preparation, and/or use of wet-milled superdisintegrants in drug suspensions and/or in drug nano-composite or composite micro-particles, which may ultimately be used in dosage forms such as tablets, capsules, powders, sachets, dry-powder inhalers, etc.

Certain embodiments of the present disclosure provide for a substantially full recovery of active agents or nanoparticles. Thus, the present disclosure is more efficient than prior known methods (e.g., methods utilizing sugar, sugar alcohols, water-soluble polymers). Further, as opposed to surfactants which cause irritation to sensory pulmonary epithelium, and may cause physical instability of drug suspensions through Ostwald ripening and agglomeration, embodiments of the present disclosure do not have these drawbacks. Thus, embodiments of the present disclosure lead to substantial benefits.

Although the systems and methods of the present disclosure have been described with reference to exemplary embodiments thereof, the present disclosure is not limited to such exemplary embodiments and/or implementations. Rather, the systems and methods of the present disclosure are susceptible to many implementations and applications, as will be readily apparent to persons skilled in the art from the disclosure hereof. The present disclosure expressly encompasses such modifications, enhancements and/or variations of the disclosed embodiments. Since many changes could be made in the above construction and many widely different embodiments of this disclosure could be made without departing from the scope thereof, it is intended that all matter contained in the drawings and specification shall be interpreted as illustrative and not in a limiting sense. Additional modifications, changes, and substitutions are intended in the foregoing disclosure. Accordingly, it is appropriate that the appended claims be construed broadly and in a manner consistent with the scope of the disclosure.

The invention claimed is:

1. A method for fabricating colloidal and ultrafine superdisintegrant (SDI) particles comprising:
providing SDI particles with sizes less than about 100 microns, as measured in the dry state;
adding the SDI particles to an aqueous solution of a steric stabilizer or soluble biopolymer to form an aqueous pre-suspension comprising from about 0.5 w/w to about 5.0% w/w of the SDI particles, wherein the steric stabilizer or soluble polymer is at a concentration sufficient to reduce interfacial tension between water and the SDI particles of the aqueous pre-suspension, said concentration of steric stabilizer or soluble polymer being at least about 1% w/w concentration in water;
adding the SDI pre-suspension to a media-mill and contacting the pre-suspension of SDI particles with milling media with sizes in the range of about 25 microns to about 4.0 mm; and
wet-milling the SDI particles in the media-mill to form colloidal and ultrafine SDI particles with a median size d50 (50 vol. % passing size) of less than about 5 microns, measured in the wet swollen state.

2. The method of claim 1, further comprising the steps of: (i) drying the suspension to form a composite of SDI and active agent particles, and (ii) incorporating the dried composite into a solid dosage form.

3. The method of claim 1, further comprising coating and drying the suspension onto an excipient via a fluidized bed processor to form a composite of SDI and active agent particles on at least a portion of the excipient.

4. The method of claim 3, wherein the drying method is selected from the group consisting of a fluidized bed coating and drying operation, spray-drying, freeze-drying, vacuum drying and oven drying.

5. The method of claim 1, further comprising combining the SDI particles with active agent particles, wherein at least a portion of the active agent particles are in powder form.

6. The method of claim 1, further comprising providing active agent particles and wherein the SDI particles and active agent particles are co-wet-milled in size reduction equipment.

7. The method of claim 6, wherein the size reduction equipment is selected from the group consisting of a wet stirred media mill, a wet ball mill, a planetary mill, and milling equipment utilizing a high pressure homogenizer.

8. The method of claim 1, wherein the SDI particles include particles selected from the group consisting of croscarmellose sodium particles, sodium starch glycolate particles, crosslinked polyvinyl pyrrolidone particles, anionic SDI particles, neutral SDI particles and combinations thereof.

9. The method of claim 1, wherein the steric stabilizer include stabilizers selected from the group consisting of cellulose derivative, and povidone.

10. The method of claim 9, wherein the steric stabilizer include stabilizers selected from the group consisting of hydroxypropylmethyl cellulose, hydroxypropyl cellulose, hydroxyethyl cellulose, methylcellulose, polyvinylpyrrolidone, and combinations thereof.

11. The method of claim 1, further comprising an anionic surfactant.

12. The method of claim 11, wherein the anionic surfactant is sodium dodecyl sulfate.

13. The method of claim 1, further comprising a polymeric surfactant.

14. The method of claim 1, wherein the water further includes a solvent.

15. A method for fabricating wet-milled superdisintegrant (SDI) particles comprising:
providing SDI particles with sizes less than about 100 microns, as measured in the dry state;
adding the SDI particles to an aqueous solution of a steric stabilizer or soluble biopolymer to form an aqueous pre-suspension comprising from about 0.5 w/w to about 5.0% w/w of the SDI particles, wherein the steric stabilizer or soluble polymer is at a concentration sufficient to reduce interfacial tension between water and the SDI particles of the aqueous pre-suspension, said concentration of steric stabilizer or soluble polymer being at least about 1% w/w concentration in water;
adding the SDI pre-suspension to a media-mill and contacting the pre-suspension of SDI particles with milling media with sizes in the range of 25 microns to about 4.0 mm; and
wet-milling the SDI particles in the mill to form SDI particles with a median size d50 (50 vol. % passing size) between about 5 to 50 microns, as measured in the wet swollen state.

16. The method of claim 15, wherein the water further includes a solvent that facilitates the dissolution of the stabilizer, biopolymer, and surfactants.

17. The method of claim 15, further comprising the steps of: (i) drying the suspension to form a composite of SDI and active agent particles, and (ii) incorporating the dried composite into a solid dosage form.

18. The method of claim 17, wherein at least a portion of the active agent particles are in powder form.

19. The method of claim 15, further comprising coating and drying the suspension onto an excipient via a fluidized bed processor to form a composite of SDI and active agent particles on at least a portion of the excipient.

20. The method of claim 19, wherein the drying method is selected from the group consisting of a fluidized bed coating and drying operation, spray-drying, freeze-drying, vacuum drying and oven drying.

21. The method of claim 15, further comprising providing active agent particles and wherein the SDI particles and active agent particles are co-wet-milled in size reduction equipment.

22. The method of claim 21, wherein the size reduction equipment is selected from the group consisting of a wet stirred media mill, a wet ball mill, a planetary mill, and milling equipment utilizing a high pressure homogenizer.

23. The method of claim 15, wherein the SDI particles include particles selected from the group consisting of croscarmellose sodium particles, sodium starch glycolate particles, crosslinked polyvinyl pyrrolidone particles, anionic SDI particles, neutral SDI particles and combinations thereof.

24. The method of claim 15, wherein the steric stabilizer include stabilizers selected from the group consisting of cellulose derivative, and povidone.

25. The method of claim 24, wherein the steric stabilizer include stabilizers selected from the group consisting of hydroxypropylmethyl cellulose, hydroxypropyl cellulose, hydroxyethyl cellulose, methylcellulose, polyvinylpyrrolidone, and combinations thereof.

26. The method of claim 15, further comprising an anionic surfactant.

27. The method of claim 26, wherein the anionic surfactant is sodium dodecyl sulfate.

28. The method of claim 15, further comprising a polymeric surfactant.

29. The method of claim 15, wherein the water further includes a solvent.

* * * * *